US011480565B2

(12) United States Patent
Nimri et al.

(10) Patent No.: US 11,480,565 B2
(45) Date of Patent: Oct. 25, 2022

(54) AUTOMATED IMMUNOASSAY

(71) Applicant: Bio-Rad Laboratories, Inc., Hercules, CA (US)

(72) Inventors: Shai Nimri, Kibbutz Nir David (IL); Yochanan Uri, Givat Ela (IL); Boaz Ran, Haifa (IL)

(73) Assignee: Bio-Rad Laboratories, Inc., Hercules, CA (US)

( * ) Notice: Subject to any disclaimer, the term of this patent is extended or adjusted under 35 U.S.C. 154(b) by 218 days.

(21) Appl. No.: 16/900,577

(22) Filed: Jun. 12, 2020

(65) Prior Publication Data

US 2021/0389305 A1    Dec. 16, 2021

(51) Int. Cl.
*G01N 33/53* (2006.01)
*B01L 3/00* (2006.01)
*G01N 35/10* (2006.01)
*G01N 35/00* (2006.01)
*G01N 33/543* (2006.01)
(Continued)

(52) U.S. Cl.
CPC ........ *G01N 33/5302* (2013.01); *B01L 3/5085* (2013.01); *B01L 3/502715* (2013.01); *G01N 21/75* (2013.01); *G01N 33/54326* (2013.01); *G01N 35/0098* (2013.01); *G01N 35/04* (2013.01); *G01N 35/10* (2013.01); *B01L 2300/0654* (2013.01);
(Continued)

(58) Field of Classification Search
CPC ......... G01N 33/5302; G01N 33/54326; G01N 35/0098; G01N 35/04; G01N 35/10; G01N 2035/0477; G01N 2035/103; G01N 21/00; G01N 2035/1062; B01L 3/502715; B01L 3/5085; B01L 2300/0654
See application file for complete search history.

(56) References Cited

U.S. PATENT DOCUMENTS 3,203,290 A * 8/1965 Ashby ................ G01N 1/06
83/915.5
4,648,262 A * 3/1987 Reis .................... G01N 11/12
73/54.18
(Continued)

FOREIGN PATENT DOCUMENTS

EP        3093649 B1    5/2019
JP     2009175771 A     8/2009
(Continued)

OTHER PUBLICATIONS

Pamme, "On-chip bioanalysis with magnetic particles," Current Opinion in Chemical Biology, Jun. 7, 2012, vol. 16, pp. 436-443.
(Continued)

*Primary Examiner* — Samuel P Siefke
*Assistant Examiner* — Henry H Nguyen
(74) *Attorney, Agent, or Firm* — Kilpatrick Townsend and Stockton LLP

(57) ABSTRACT

An instrument for detecting signal from a biological sample includes a pipettor module configured to hold a plurality of pipettes in respective pipette positions, to hold liquid in one or more pipette tips, and to pipette liquid in and out of the one or more pipette tips. Each of the one or more pipette tips has a pipette tip point. The instrument further includes one or more magnets positioned such that each of the one or more pipette tips is adjacent one of the one or more magnets.

15 Claims, 21 Drawing Sheets

(51) Int. Cl.
*G01N 35/04* (2006.01)
*G01N 21/75* (2006.01)

(52) U.S. Cl.
CPC ............ *G01N 2035/0477* (2013.01); *G01N 2035/103* (2013.01); *G01N 2035/1062* (2013.01)

(56) References Cited

U.S. PATENT DOCUMENTS

| | | | |
|---|---|---|---|
| 5,647,994 A | 7/1997 | Tuunanen et al. | |
| 6,187,270 B1 | 2/2001 | Schmitt et al. | |
| 6,398,364 B1 | 6/2002 | Bryars | |
| 8,557,599 B2 | 10/2013 | Koyata et al. | |
| 9,671,342 B2 | 6/2017 | Gambini et al. | |
| 10,151,929 B2 | 12/2018 | Deguenther et al. | |
| 2006/0133965 A1* | 6/2006 | Tajima | G01N 35/1009 422/63 |
| 2007/0242344 A1 | 10/2007 | Pan | |
| 2007/0263210 A1* | 11/2007 | Taguchi | G01N 21/645 356/318 |
| 2008/0190458 A1 | 8/2008 | Garcia Gros et al. | |
| 2010/0060893 A1 | 3/2010 | Norton et al. | |
| 2013/0026079 A1 | 1/2013 | Davis et al. | |
| 2014/0165645 A1* | 6/2014 | Schryver | B01L 7/00 219/535 |
| 2014/0273277 A1 | 9/2014 | Diamond et al. | |
| 2016/0180998 A1 | 6/2016 | Kanai et al. | |
| 2018/0156732 A1* | 6/2018 | Tajima | G01N 21/64 |
| 2019/0011885 A1 | 1/2019 | Durr et al. | |

FOREIGN PATENT DOCUMENTS

| | | |
|---|---|---|
| JP | 5242454 B2 | 4/2013 |
| JP | 2019/045271 A | 3/2019 |
| KR | 101965701 B1 | 4/2019 |

OTHER PUBLICATIONS

Gijs et al., "Microfluidic Applications of Magnetic Particles for Biological Analysis and Catalysis," Chem. Rev. Dec. 4, 2009, vol. 110, No. 3, pp. 1518-1563.

Hayes et al., "Flow-Based Microimmunoassay," Anal. Chem. Nov. 10, 2001, vol. 73, No. 24, pp. 5896-5902.

International Search Report and Written Opinion in PCT/US2021/036667 dated Nov. 3, 2021; 13 pages.

\* cited by examiner

AREA ENLARGED IN FIG. 18

AUTOMATED IMMUNOASSAY

BACKGROUND OF THE INVENTION

An immunoassay is a procedure for detecting or measuring proteins or other substances, generally through their properties as antigens or antibodies. The substance detected or measured may be called an "analyte". Immunoassays are often used in biological and medical research, or for disease detection and monitoring, but have other uses as well.

In a "sandwich" immunoassay, a substrate is coated with antibodies designed to bind with a specific protein or other substance of interest. The substrate is flooded with a solution containing the specific protein, which binds to the antibodies on the substrate. The antibodies on the substrate are often called "capture" antibodies.

Once the protein of interest has had a chance to bind to the capture antibodies, the substrate may be washed, and flooded with another solution containing different antibodies called "detection" antibodies, also designed to bind with the protein of interest. The detection antibodies may be labeled with an easily-detectable marker, for example a chemiluminescent substance. Once the detection antibodies have had a chance to bind with the proteins of interest, the substrate may be washed, leaving behind mainly the protein of interest "sandwiched" between the capture antibodies and the detection antibodies. The strength of the luminescent signal from the chemiluminescent markers is then measured, and indicates the presence and concentration of the protein of interest.

Performing an immunoassay is a common procedure performed manually on a daily basis in many research labs. This procedure may be tedious, time-consuming, and prone to user error. Therefore, improved methods and equipment for performing immunoassays, in which at least some of the protocol steps are automated, are desired.

BRIEF SUMMARY OF THE INVENTION

According to one aspect, an instrument for detecting signal from a biological sample comprises a pipettor module configured to hold a plurality of pipettes in respective pipette positions, to hold liquid in one or more pipette tips, and to pipette liquid in and out of the one or more pipette tips. Each of the one or more pipette tips has a pipette tip point. The instrument further comprises a magnet module holding one or more magnets, the magnet module coupleable and decoupleable from the pipettor module such that when the magnet module is coupled to the pipettor, each of the one or more pipette tips is adjacent one of the one or more magnets. In some embodiments, the instrument comprises exactly one magnet for each pipette tip position. In some embodiments, the instrument further comprises an optical detection module positioned to detect an optical signal from particles magnetically fixed to respective sides of the one or more pipette tips by the one or more magnets. In some embodiments, the instrument further comprises one or more mirrors positioned such that the optical signal from each or the one or more pipette tips is reflected from one of the one or more mirrors and directed at an angle substantially parallel to the orientation of the pipette tips and in the direction of the pipette tip points. In some embodiments, the optical signals are reflected directly from the one or more mirrors to the optical detection module without any further reflections. In some embodiments, the one or more mirrors are one or more first mirrors, and the instrument further comprises a second mirror positioned under the pipette tip points that redirects the optical signal from the one or more first mirrors to the optical detection module. In some embodiments, the instrument comprises two or more second mirrors, each of the two or more second mirrors reflecting optical signal from a subset of the pipette tips. In some embodiments, the optical detection module comprises a camera positioned to receive optical signal reflected from the second mirror. In some embodiments, the optical detection module has only one camera positioned to receive optical signal originating from each or the one or more pipette tips. In some embodiments, the optical detection module has a plurality of cameras, and each or the plurality of cameras is positioned to receive optical signal originating from only a subset of the pipette tips. In some embodiments, there are fewer first mirrors than pipette tip positions, and at least some of the first mirrors reflect optical signal from more than one of the one or more pipette tips. In some embodiments, the instrument comprises a plurality of pipette tips disposed in a line or in a two-dimensional array, and the pipettor module is configured to hold and pipette liquid in and out of the plurality of pipette tips simultaneously. In some embodiments, the magnet module further comprises one or more spring clips, one spring clip respectively for each of the one or more magnets, the one or more spring clips positioned to hold the one or more magnets against the pipette tips. In some embodiments, the instrument further comprises a magnet module coupling station where the magnet module is coupled to the pipettor module, the magnet module coupling station comprising one or more posts positioned to deflect the one or more magnets away from the one or more pipettes against the action of the one or more spring clips during coupling of the magnet module to the pipettor module. In some embodiments, the instrument further comprises a motorized mechanism configured to move the pipettor module into and out of the magnet module coupling station to automatically couple the magnet module to the pipettor module. In some embodiments, the instrument further comprises one or more optical detection modules positioned to detect an optical signal from particles magnetically fixed to respective sides of the one or more pipette tips by the one or more magnets, and one or more mirrors positioned such that the optical signal from each or the one or more pipette tips is reflected from one of the one or more mirrors and directed at an angle substantially parallel to the orientation of the pipette tips and in the direction of the pipette tip points, the one or more mirrors disposed at a detection station, and the motorized mechanism is further configured to move the coupled pipettor module and magnet module to the detection station. In some embodiments, the instrument further comprises a reagent loading station, and the motorized mechanism is further configured to move the pipettor module to the reagent loading station. In some embodiments, the instrument further comprises a shaker for agitating liquids present at the reagent loading station.

According to another aspect, a method of automatically performing an assay comprises loading a plurality of pipette tips onto a pipettor from a rack, docking a magnet array to the pipettor, and loading a liquid carrying magnetic beads comprising capture antibodies with specifically bound analyte molecules into the pipette tips using the pipettor, such that beads in at least some of the pipette tips clump near respective magnets of the magnet array. In some embodiments, docking the magnet array to the pipettor comprises moving the pipettor to a magnet module coupling station. In some embodiments, docking the magnet array to the pipettor comprises automatically moving the magnets in the magnet array away from the paths of the pipette tips. In some embodiments, the method further comprises reflecting, using at least one mirror, light emanating from detectible tags on the magnetic beads toward an optical detection system, and imaging the light with the optical detection system. In some embodiments, the method further comprises moving the pipette tips to be adjacent the one or more mirrors. The method may further comprise loading detection antibodies into the pipette tips to bind with the analyte molecules, and adding a signal-forming reagent to the pipette tips, the signal-forming reagent including the detectable tags. In some embodiments, the method comprises loading detection antibodies into the pipette tips to bind with the analyte molecules, the detection antibodies also carrying the detectable tags.

DETAILED DESCRIPTION OF THE INVENTION

Embodiments of the invention provide methods and equipment for performing immunoassays and other biochemical procedures.

Figure 1:
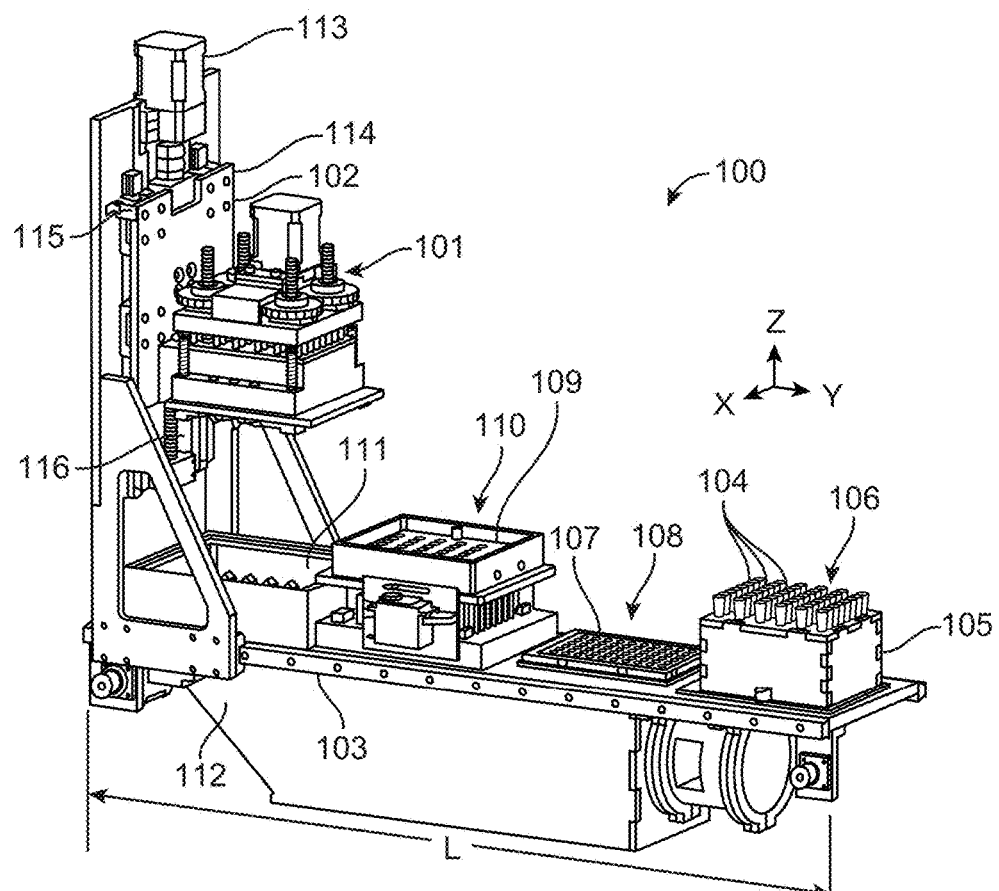
FIG. 1 illustrates an instrument for performing immunoassays and other analyses, in accordance with embodiments of the invention.

FIG. 1 illustrates an instrument 100 for performing immunoassays and other analyses, in accordance with embodiments of the invention. In this example, instrument 100 can perform a number of assays substantially automatically and in parallel, improving the efficiency of the assays.

Instrument 100 includes a pipettor module 101 capable of holding a number of standard pipette tips, and capable of pipetting liquid in and out of the pipette tips in parallel. Pipettor module 101 is explained in more detail below.

Pipettor module 101 is mounted on a Z-axis mechanism 102, which can raise and lower pipettor module 101 in the Z direction illustrated in FIG. 1. Z-axis mechanism 102 is preferably motorized using a motor 113. Motor 113 may conveniently be a stepper motor, but other kinds of motors may be used. A mounting plate 114 is carried on linear bearings 115, and moved by a leadscrew 116, driven by motor 113. Z-axis mechanism 102 is further mounted on a Y-axis mechanism 103, also preferably motorized, which can move Z-axis mechanism 102 and pipettor module 101 back and forth in the Y direction. Thus, working in concert under the control of a computerized controller, Z-axis mechanism 102 and Y-axis mechanism 103 can cause pipettor module 101 to visit and interact with a number of stations along the length L of instrument 100.

For example, in the embodiment of FIG. 1, a number of pipette tips 104 have been prearranged in a tip rack 105 at a tip loading station 106. Pipette tips 104 are preferably standard pipette tips, although this is not a requirement, and may be disposable. In this example, 48 pipette tips 104 are provided, in six rows having eight pipettes 104 in each row, but more or fewer pipette tips 104 may be used, including a single pipette tip. In instrument 100, pipette tips 104 are spaced 9 mm apart along the rows, and the rows are spaced 18 mm apart, but other spacings may be used, so long as they are compatible with other components of the system.

A reagent plate 107 is has been prearranged at a reagent loading station 108. Reagent plate 107 may be a standard reagent plate, having wells in rows and columns spaced 4.5 mm or 9 mm apart, although other spacings may be used in other embodiments. The wells may conveniently be space 9 mm apart along the rows, and the rows conveniently spaced 18 mm apart, or a multiple or submultiple of 9 mm, as is common in the art. Pipette tips 104 are spaced the same as at least some of the wells in reagent plate 107.

Figure 2:
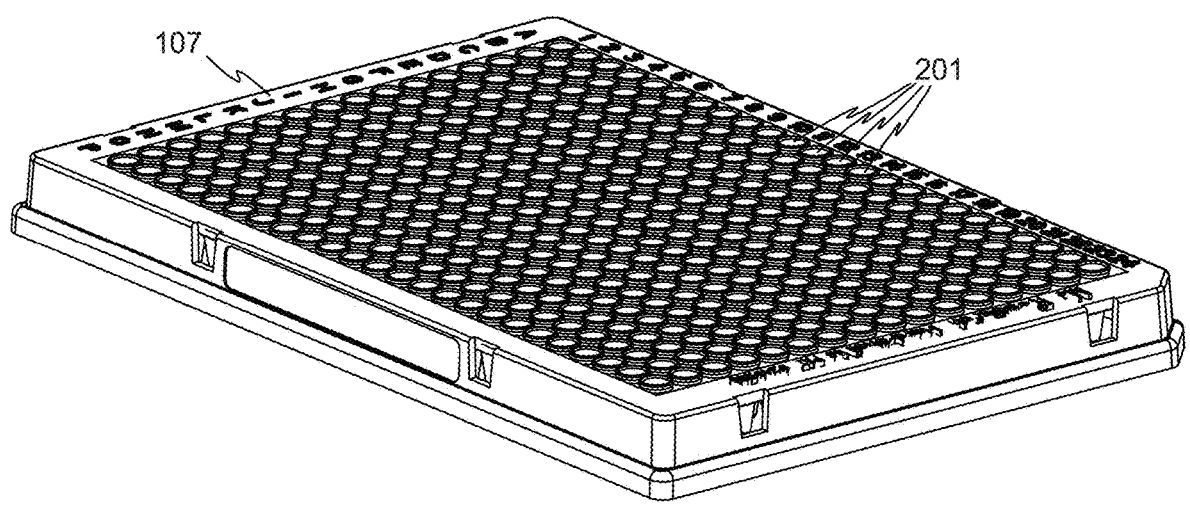
FIG. 2 illustrates a reagent plate in accordance with embodiments of the invention.

FIG. 2 illustrates reagent plate 107 in more detail. In this example, reagent plate 107 includes 384 wells 201, in 24 rows having 16 wells in each row. Wells 201 are spaced 4.5 mm (a submultiple of 9 mm) apart in both directions. Pipette tips 104 can thus access 48 of the wells 201 of reagent plate 107 simultaneously. Reagent plate 107 may have more wells 201 than there are pipette tips 104, as in this example, for any number of reasons. For example, the fluid containing the analyte to be detected or measured may be placed in one subset of wells 201, one or more washing fluids may be placed in other subsets of wells 201, and a fluid containing detection antibodies may be placed in yet another subset of the wells. Y-axis mechanism 103 can preferably position pipettor module 101 over different subsets of wells as needed at different stages of an assay. In some embodiments, an X-axis mechanism may be present for moving pipettor 101 and pipette tips 104 back and forth in the X direction, so that additional wells of reagent plate 107 can be accessed by pipette tips 104.

In any event, at least some of wells 201 are filled with fluid, for example a solution containing the analyte to be detected or measured. In addition, magnetic beads may be added to the fluid. The magnetic beads are coated with capture antibodies designed to bind with the analyte, and may provide the substrate to be used in the immunoassay. Suitable magnetic beads are available from Bio-Rad Laboratories, Inc. of Hercules, Calif., USA. The beads may be of any workable size, but in some embodiments are about 5.0 to 8.0 microns in diameter, so that they may suspend readily in the fluid in wells 201.

Referring again to FIG. 1, reagent plate station 108 may include a shaker or other mechanism (not shown) for agitating the fluid in wells 201, for example for the capture step of an immunoassay, in which the analyte is encouraged to bind with the capture antibodies on the magnetic beads.

Instrument 100 further includes a magnet module 109 positioned at a magnet module coupling station 110. Magnet module 109 and its use are described in more detail below.

Instrument 100 further includes a mirror module 111, also to be described in more detail below. An imaging system is provided in base 112 of instrument 100.

Figure 3A:
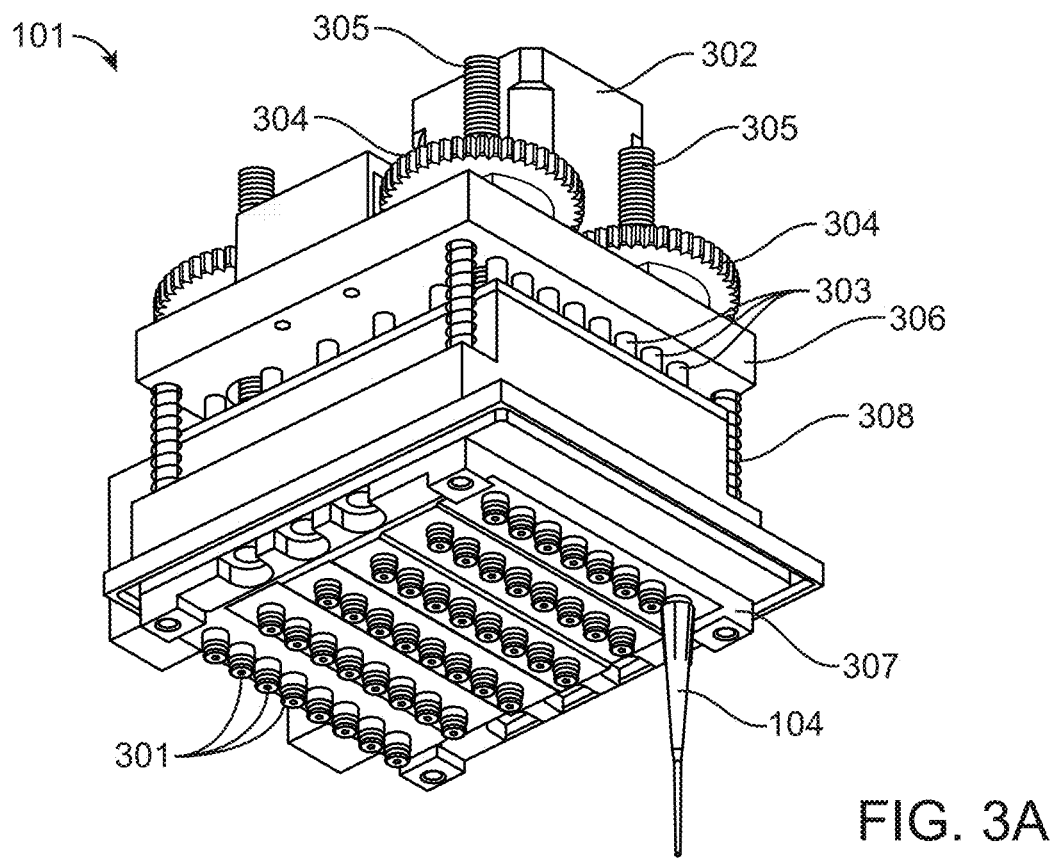
FIGS. 3A and 3B show lower and upper oblique views of a pipettor module in accordance with embodiments of the invention.
Figure 3B:
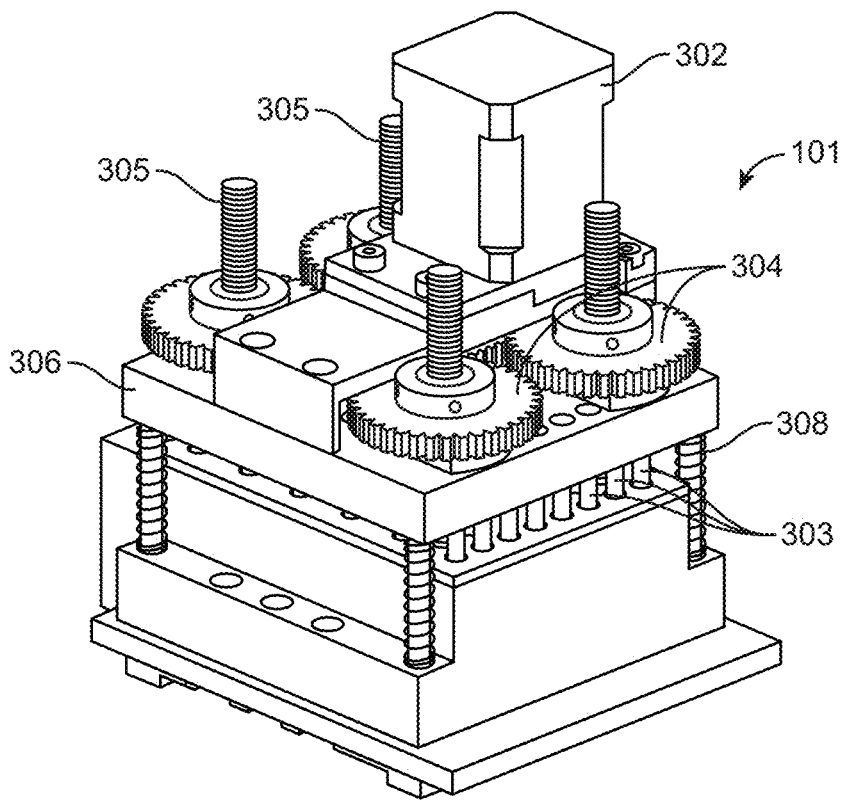

FIGS. 3A and 3B show lower and upper oblique views of pipettor module 101 in more detail, in accordance with embodiments of the invention. Pipettor module 101 includes an array of connectors 301 for mounting pipette tips 104. One of pipette tips 104 is shown in FIG. 3A, coupled to one of connectors 301. Connectors 301 are preferably made of a durable material, for example stainless steel, a hard plastic such as polyether ether ketone ("PEEK"), or another suitable material. The connectors are sized to grip the inside of a pipette tip 104 when the pipette tip 104 and the connector 301 are pushed together. The tips 104 may have an inner ridge or lip that deforms in contact with the connectors 301 to achieve a good seal. Each of connectors 301 has a longitudinal passage for the passage of air.

A motor 302, for example a stepper motor, drives a number of plungers 303 via a set of gears 304 and leadscrews 305. Each of plungers 303 is configured to draw air into and push air out of one of pipette tips 104. Plungers 303 are anchored to drive plate 306, and so move as a unit, so that fluid can be simultaneously pipetted via pipette tips 104, from all of the wells 201 that are in use. An ejector plate 307 is actuated when drive plate 306 is driven downward beyond the range used for pipetting onto ejector rods 308. Ejector plate 307 can be used to strip pipette tips 104 from the connectors 301 at the end of an assay, for disposal.

Figure 4:
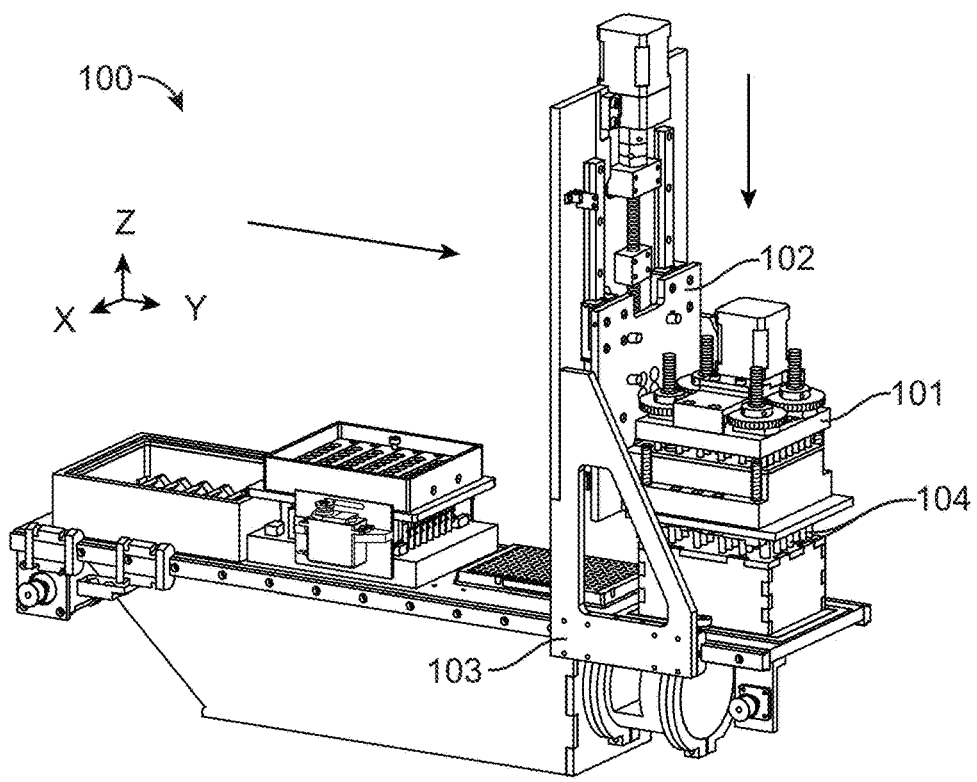
FIG. 4 illustrates a step in performing an assay, in accordance with embodiments of the invention.

As shown in FIG. 4, to begin an assay (once the analyte has been given a chance to bind to the capture antibodies on the magnetic beads in wells 201 of reagent plate 107), Y-axis mechanism 103 and Z-axis mechanism 102 are driven to position pipettor module 101 over previously-positioned pipette tips 104, and to lower pipettor module 101 onto pipette tips 104, loading pipette tips 104 onto connectors 301 of pipettor module 101.

Figure 5:
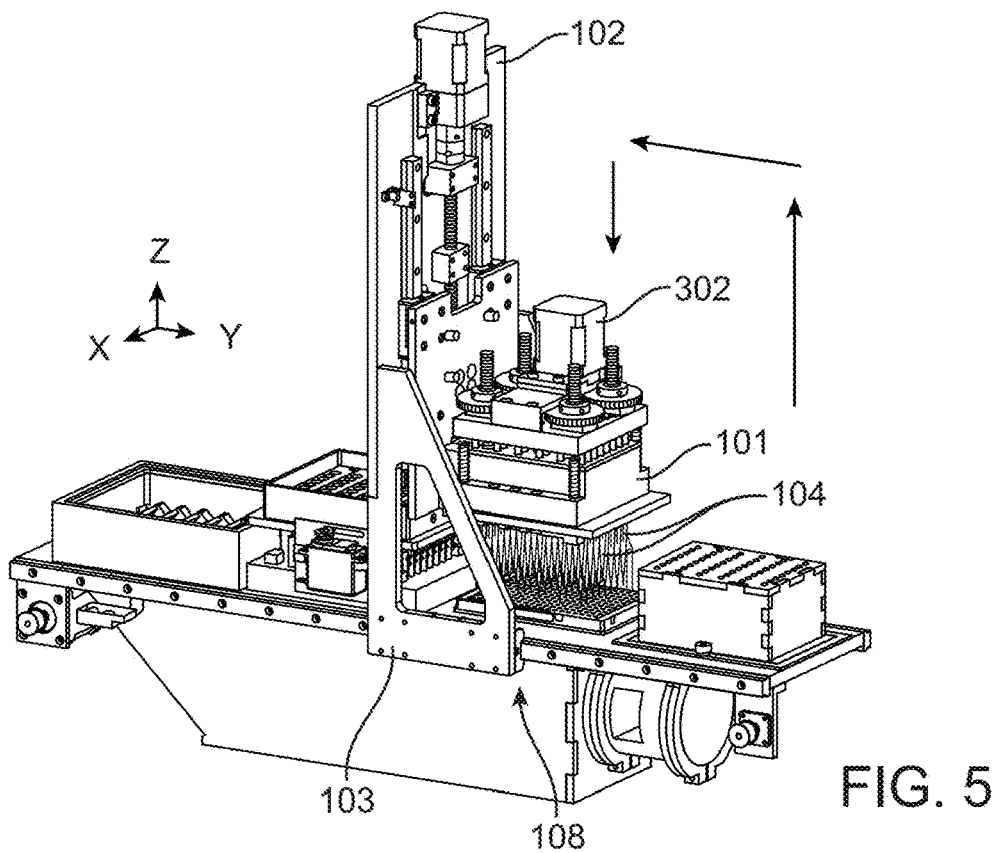
FIG. 5 illustrates another step in performing an assay, in accordance with embodiments of the invention.

As shown in FIG. 5, pipettor module 101 and pipette tips 104 are then lifted by Z-axis mechanism 102, positioned over reagent plate 107 by Y-axis mechanism 103, and lowered so that pipette tips 104 reach the fluid in wells 201 of reagent plate 107. Fluid from reagent plate 107 is then pipetted into pipette tips 104, by turning motor 302 of pipettor module 101, to draw fluid into pipette tips 104.

Figure 6:
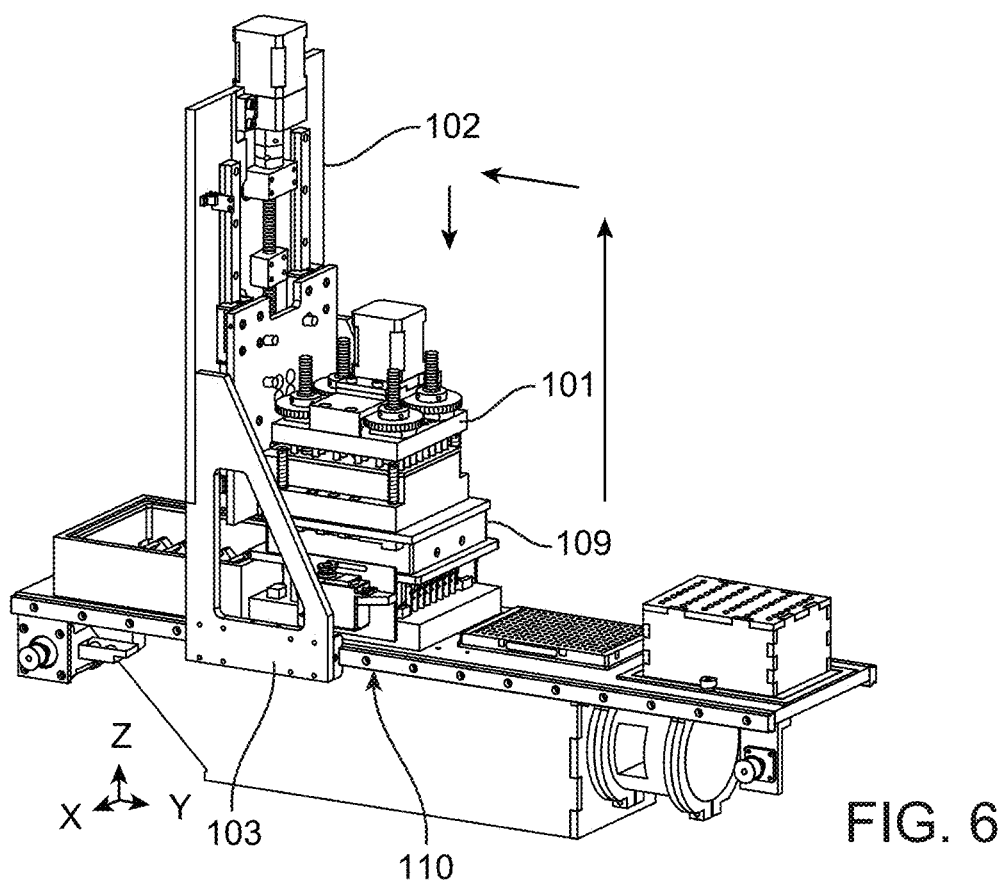
FIG. 6 illustrates another step in performing an assay, in accordance with embodiments of the invention.

Once fluid is in pipette tips 104, Y-axis mechanism 103 and Z-axis mechanism 102 are driven to lift pipette tips 104 out of reagent plate 107, and place them in magnet module 109 at magnet module coupling station 110, as shown in FIG. 6.

Figure 7A:
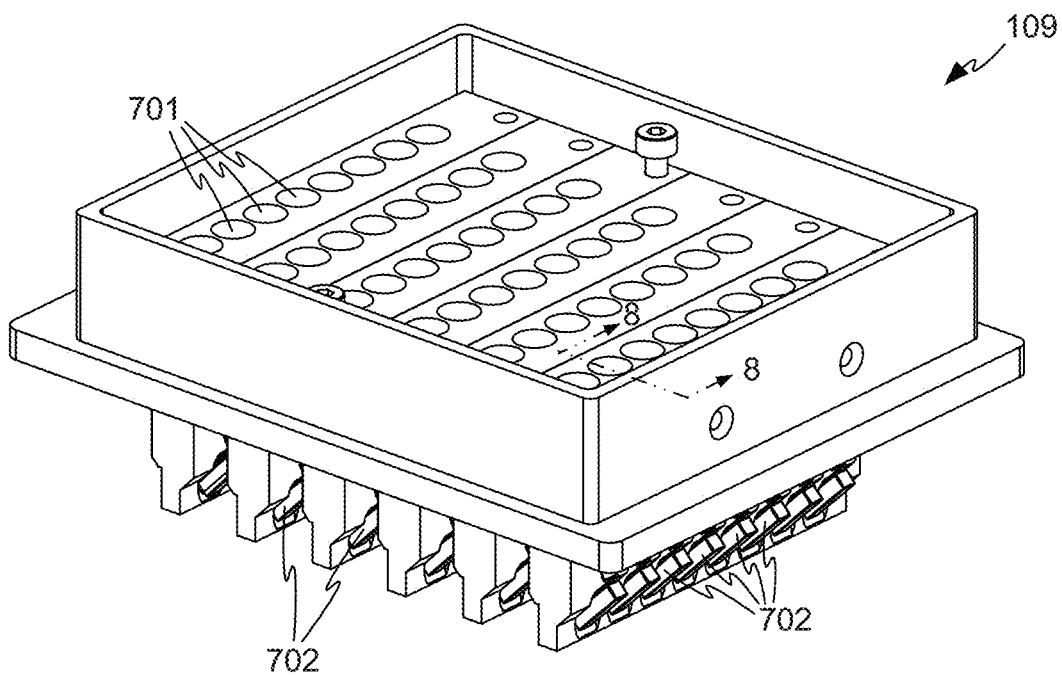
FIGS. 7A and 7B show upper and lower oblique views of a magnet module, in accordance with embodiments of the invention.
Figure 7B:
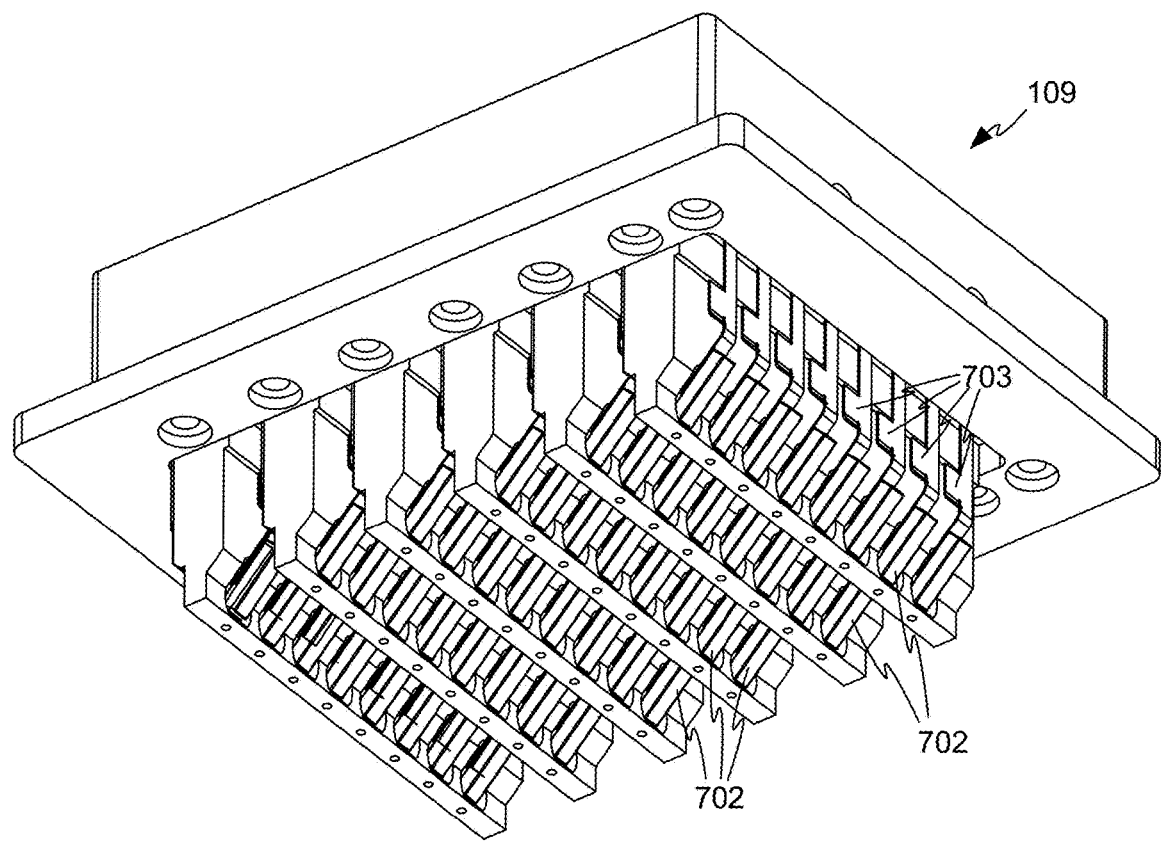

FIGS. 7A and 7B show upper and lower oblique views of magnet module 109, in accordance with embodiments of the invention. Magnet module 109 includes an array of holes 701 for receiving pipette tips 104. Magnet module 109 also includes an array of magnets 702, one magnet 702 for each of the expected pipette tips 104. As is visible in FIG. 7B, each of magnets 702 is mounted on a respective leaf spring 703.

Figure 8:
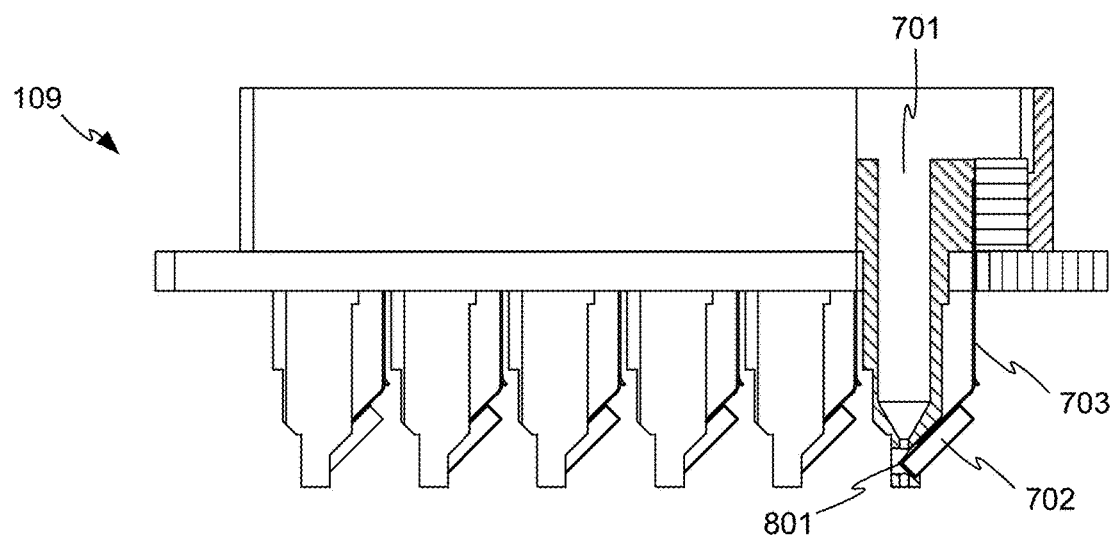
FIG. 8 is a section view of the magnet module of FIG. 7.

FIG. 8 is a section view of magnet module 109, illustrating the relationship of one of holes 701 with its respective magnet 702 and leaf spring 703. Leaf spring 703 holds magnet 702 toward the axis of hole 701, so that one corner 801 of magnet 702 protrudes into hole 701 when no pipette tip 104 is present.

Figure 9:
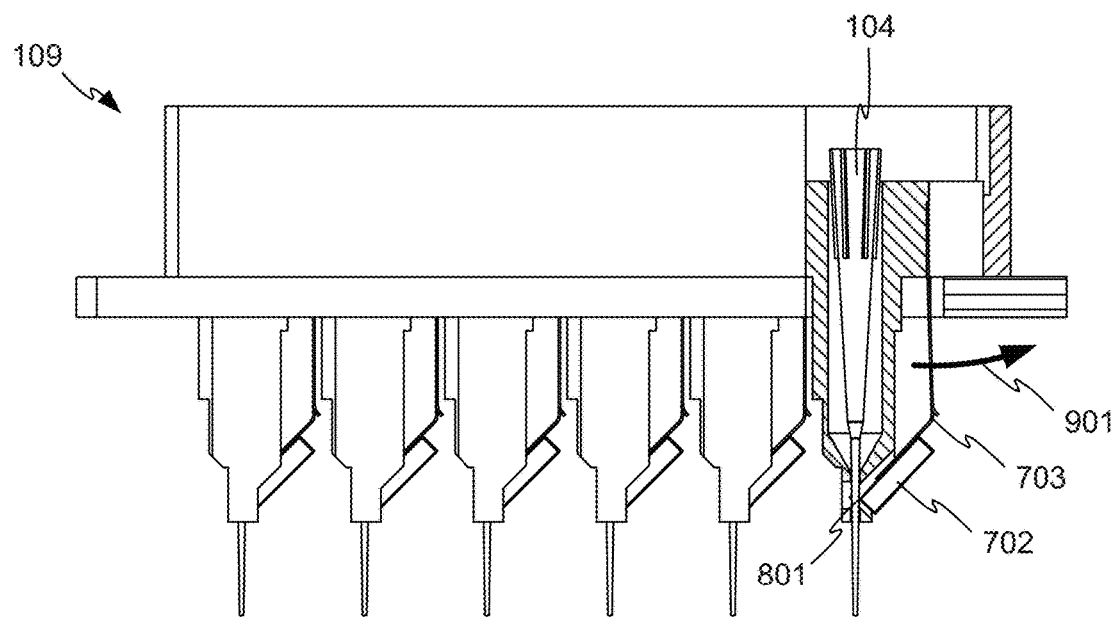
FIG. 9 shows additional details of the magnet module of FIG. 7.

FIG. 9 shows the relationship of magnet 702 and leaf spring 703 to a pipette tip 104 when pipette tip 104 is inserted into hole 701. Leaf spring 703 has deflected away from hole 701, as shown at 901, and magnet 701 now presses against pipette tip 104 at magnet corner 801.

One other feature of magnet module coupling station 110 is a mechanism for preventing damage to the tips of pipette tips 104 as they are inserted into magnet module 109, as well as preventing contamination of the magnets by the used tips when the tips are retracted from the magnet module. As is apparent from FIGS. 8 and 9, each of magnets 702 obstructs part of the respective hole 701 when no pipette tip 104 is present, so that a pipette tip 104 would collide with magnet 702 as it is inserted into magnet module 109, absent any other mechanism for avoiding the collision.

Figure 10:
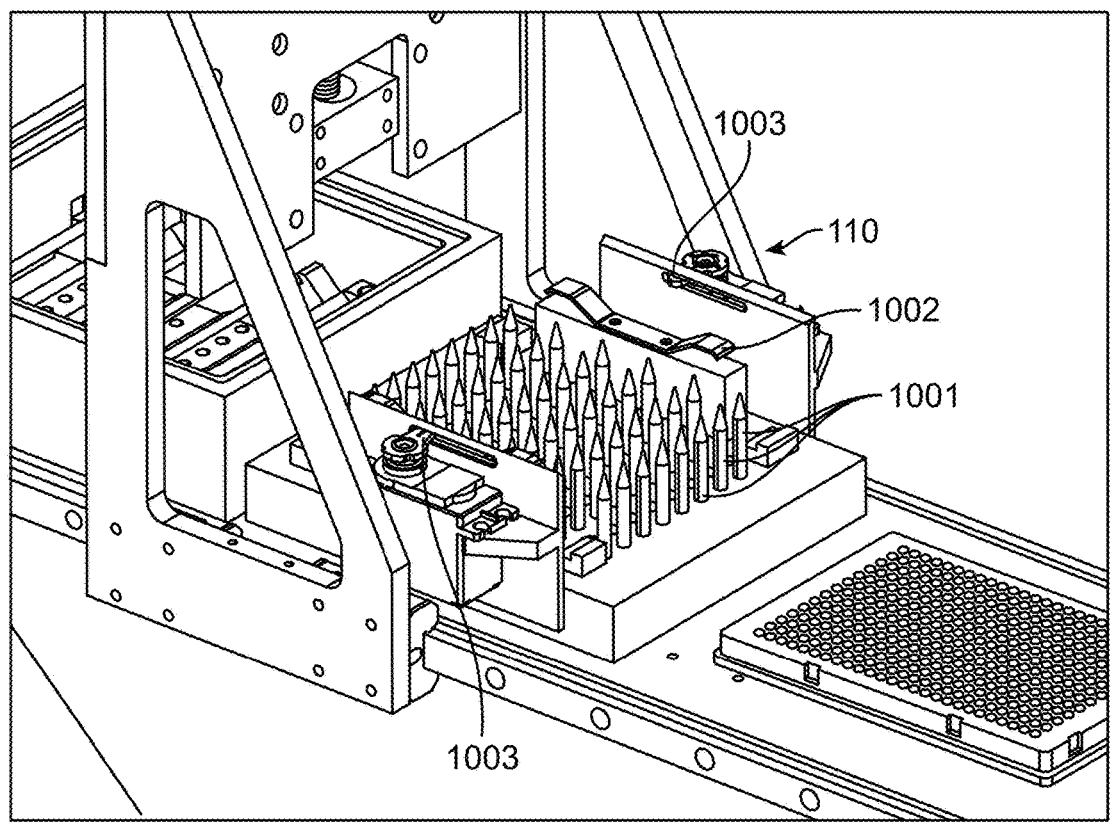
FIG. 10 illustrates a mechanism for avoiding damage to pipette tips when loading them into the magnet module of FIG. 7, as well as preventing contamination of the magnets by used tips, in accordance with embodiments of the invention.

FIG. 10 illustrates one such mechanism, in accordance with embodiments of the invention. FIG. 10 is a close-up view of magnet module coupling station 110, with magnet module 109 removed. In this embodiment, magnet module coupling station 110 includes a number of vertical tapered posts 1001, one tapered post 1001 for each expected pipette tip 104. Tapered posts 1001 interact with leaf springs 703 to draw magnets 702 away from the axes of holes 701, permitting insertion of pipette tips 104 into magnet module 109 without potential damage. This also permits removal of the used pipette tips from the magnets module without any contact of the wetted section of the tip with the magnet. Without such a mechanism, the used tips may contaminate the magnets and in turn contaminate newly inserted tips. Withdrawing the tip without first retracting the magnet may also drag the magnetic beads out of the tip and on to the magnet, which would contaminate any subsequent experiment.

Figure 11:
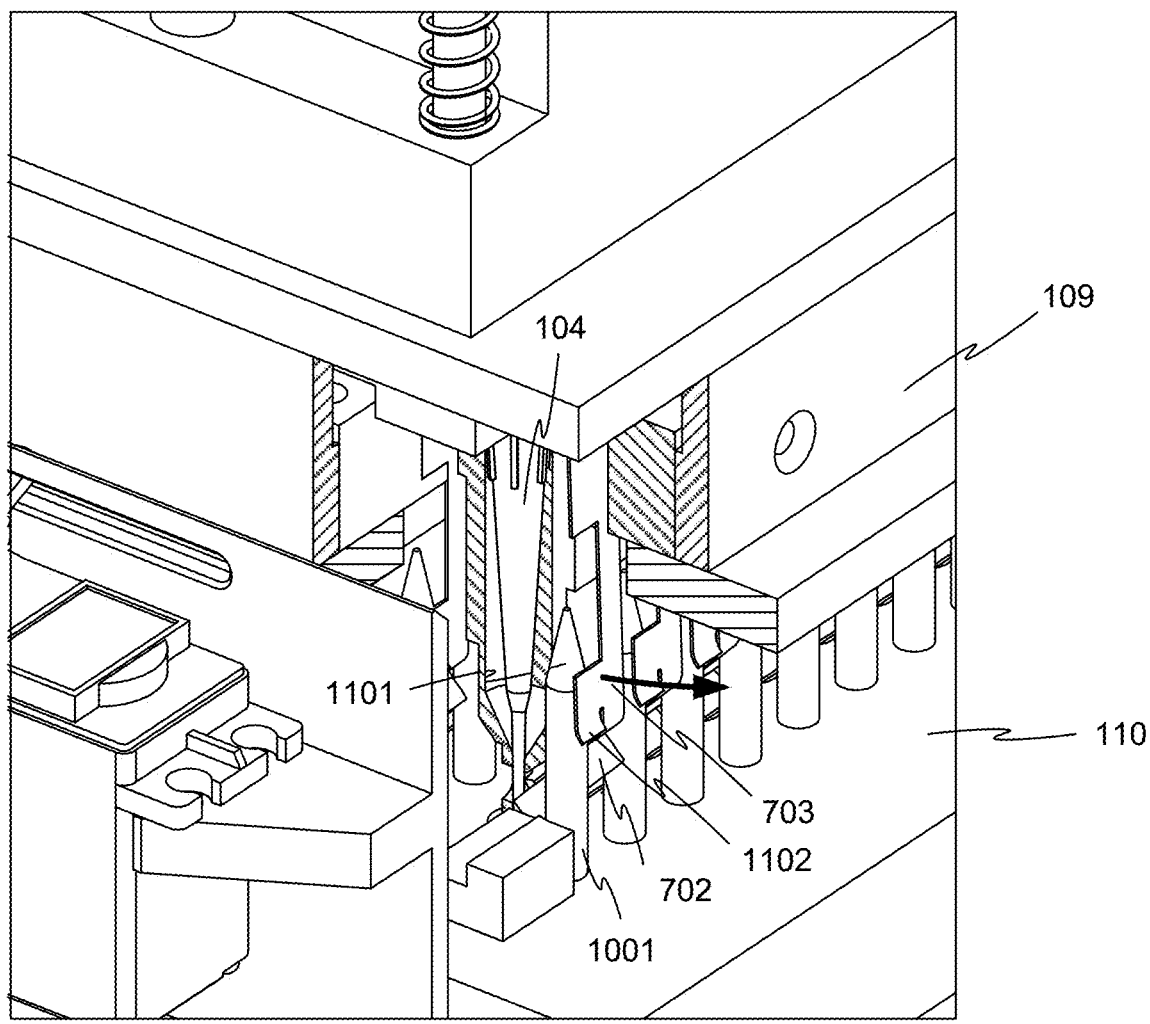
FIG. 11 shows the coupling of pipette tips to the magnet module of FIG. 7 in more detail.

This interaction is shown in more detail in FIG. 11. Tapered tip 1101 of post 1001 interacts with flared flange 1102 of leaf spring 703 as magnet module 109 is placed on magnet module coupling station 110.

Pipette tips 104 can then be inserted safely. Once magnet module 109 is withdrawn from magnet module coupling station 110, leaf springs 703 are free to urge magnets 702 against pipette tips 104.

Once magnet module 109 is coupled to pipettor 101 and pipette tips 104, they remain coupled for the remainder of the procedure. Pipettor 101 and magnet module 109 can be withdrawn from magnet module coupling station 110 as a unit, including pipette tips 104. Magnet module 109 may be coupled to pipettor 101 in any suitable way, but in some embodiments, may be coupled using docking magnets (not shown). Referring again to FIG. 10, springs 1002 may be provided to define the position of the magnet module in the Z axis by pressing it upwards against the retainer 1003 and prevent any backlash. This assists in coupling and decoupling of the magnet module while preventing shocks. In addition, movable retainers 1003 may be provided for holding magnet module 109 to magnet module coupling station 110 when it is desired to separate magnet module 109 from pipettor 101.

Figure 12:
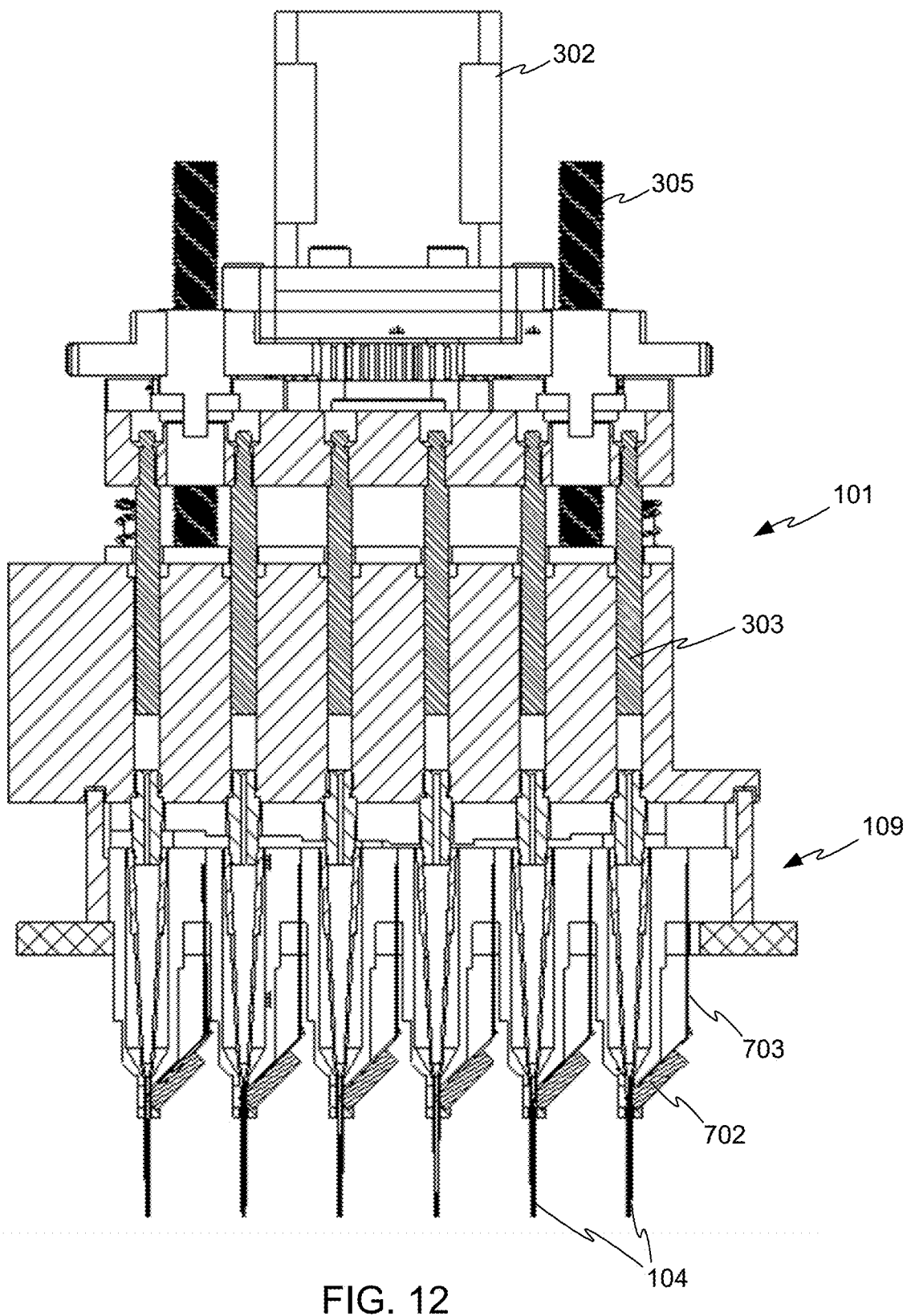
FIG. 12 shows a cross section view of the pipettor of FIGS. 3A and 3B and the magnet module of FIG. 7, coupled and holding pipette tips, in accordance with embodiments of the invention.

FIG. 12 shows a cross section view of pipettor 101 and magnet module 109, coupled and holding pipette tips 104. FIG. 12 is shown from the same direction as FIG. 8. Components labelled in FIG. 12 include motor 302, a plunger 303, a leadscrew 305, a magnet 702, and a spring clip 703.

Pipette tips 104 contain liquid including the analyte to be detected or measured, and the magnetic beads to which the analyte is bound. Because magnet 702 is in close proximity to a wall of pipette tip 104, at least some of the magnetic beads are drawn to magnet corner 801, and are held there by the strength of magnet 702.

Figure 13:
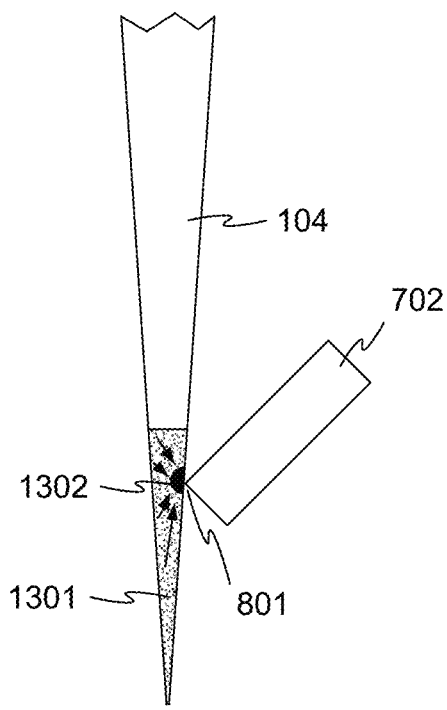
FIG. 13 illustrates the capture of magnetic beads in pipette tips, in accordance with embodiments of the invention.

FIG. 13 illustrates this condition schematically. In FIG. 13, pipette tip 104 contains liquid 1301, and is in contact with corner 801 of magnet 702. Magnetic beads in liquid 1301 are attracted to magnet 702, and form a concentrated clump of beads 1302. With the magnetic beads captured in this way, other steps of the immunoassay can be performed on the beads while they reside in pipette tips 104. For example, excess liquid 1301 may be expelled, various washing fluids may be pipetted into pipette tips 104 and expelled to cleanse beads 1302. In some embodiments, the washing fluids may be obtained by revisiting reagent plate 107 and pipetting the washing fluids from another subset of wells 201 in reagent plate 107. In another example, a solution containing the detection antibodies may be pipetted into pipette tips 104 and held for a period of time for the detection antibodies (including chemiluminescent or other optical markers) to bind to the beads 1302. The fluid containing the detection antibodies may also be obtained from yet another subset of wells 201 in reagent plate 107. Alternatively, reagent plate 107 may be replaced one or more times during an immunoassay, to provide different fluids to the system. In other embodiments, the system may be extended to have any number of reagent plates to allow fully automated workflow without having to replace plates during an experiment.

It will be recognized that the steps of an immunoassay may be performed in different orders in different embodiments of the invention. For example, as described above, the detection antibodies are introduced after the magnetic beads have been captured in pipette tips 104. In other embodiments, the detection antibodies may be bound to the magnetic beads in reagent plate 107, before magnet module 109 is attached to pipettor 101. Many variations are possible.

Figure 14:
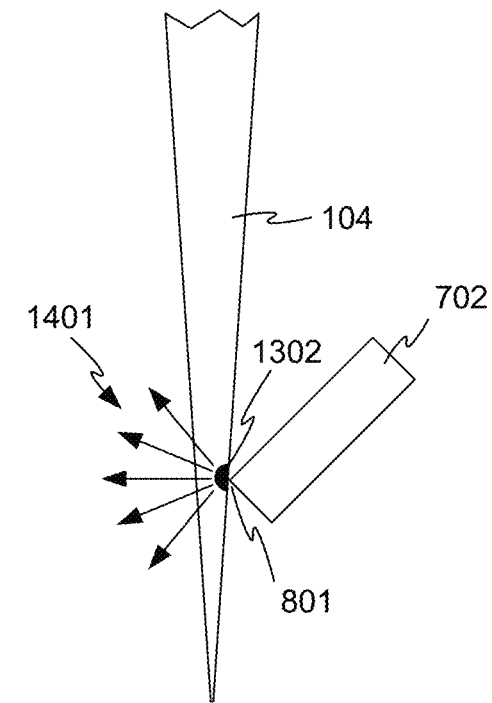
FIG. 14 illustrates optical signal emanating from the captured beads of FIG. 13.

After the clump of magnetic beads 1302 has been captured within pipette tip 104, and the detection antibodies have been bound, including their chemiluminescent or other optical markers, pipette tip 104 may appear as in FIG. 14. As shown in FIG. 14, the excess fluid has been removed from pipette tip 104.

Figure 15:
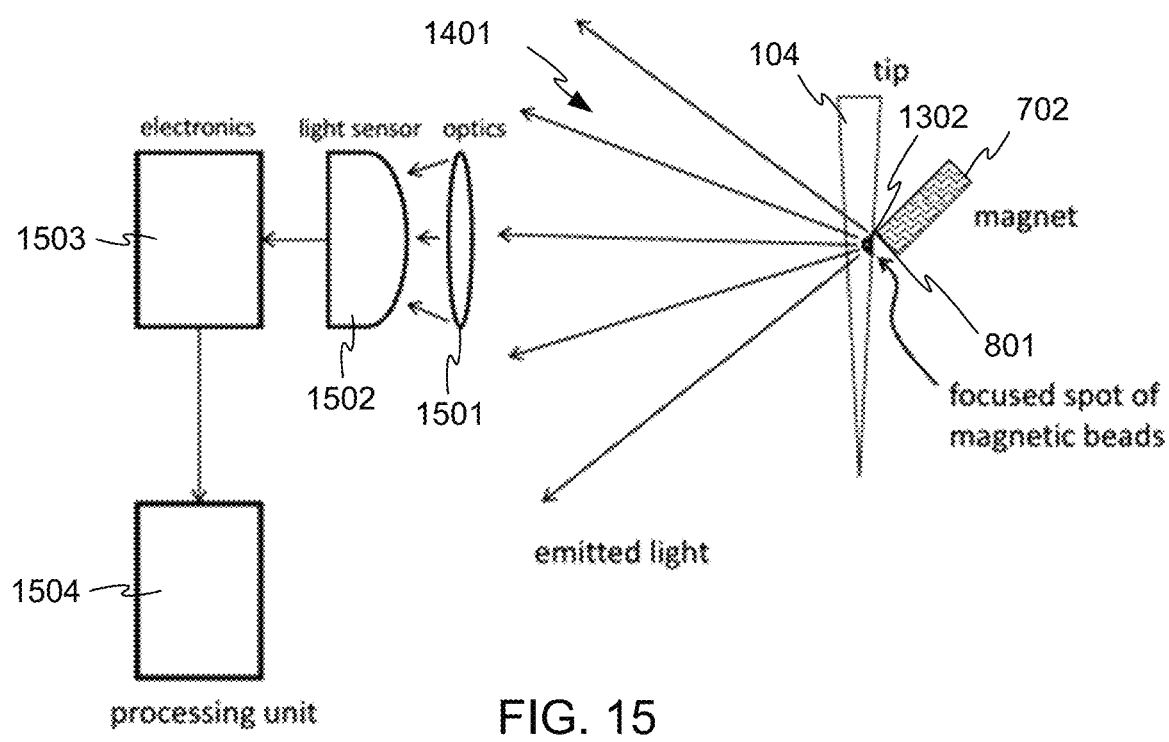
FIG. 15 illustrates a basic technique for sensing and quantifying light, in accordance with embodiments of the invention.

The presence and intensity of light 1401 indicate the presence and concentration of the analyte of interest. FIG. 15 illustrates a basic technique for sensing and quantifying light 1401 emanating from a single pipette tip 104. Some of the light 1401 is gathered by imaging optics such as a lens 1501, and is redirected to an optical sensor 1502. Optical sensor 1502 may be, for example, a phototransistor, a photodiode, a photomultiplier tube, and element of an electronic array light sensor such as a charged coupled device (CCD) sensor or a complementary metal oxide semiconductor (CMOS) sensor, or another kind of light sensor. Electronics 1503 converts the output of sensor 1502 to a numerical value. Electronics 1503 may include, for example, an analog-to-digital converter, one or more amplifiers, or other kinds of electronics. The output of electronics 1503 may be sent to a processing unit 1504 for storage, display, analysis, or other purposes. Processing unit 1504 may be, for example, a desktop computer or similar device.

A feature of some embodiments of the invention is the ability to perform several assays in parallel. It is desirable to sense the result of the multiple assays in parallel as well. While one option would be to provide every pipette tip 104 with a light sensor, this would be cumbersome and expensive.

Figure 16:
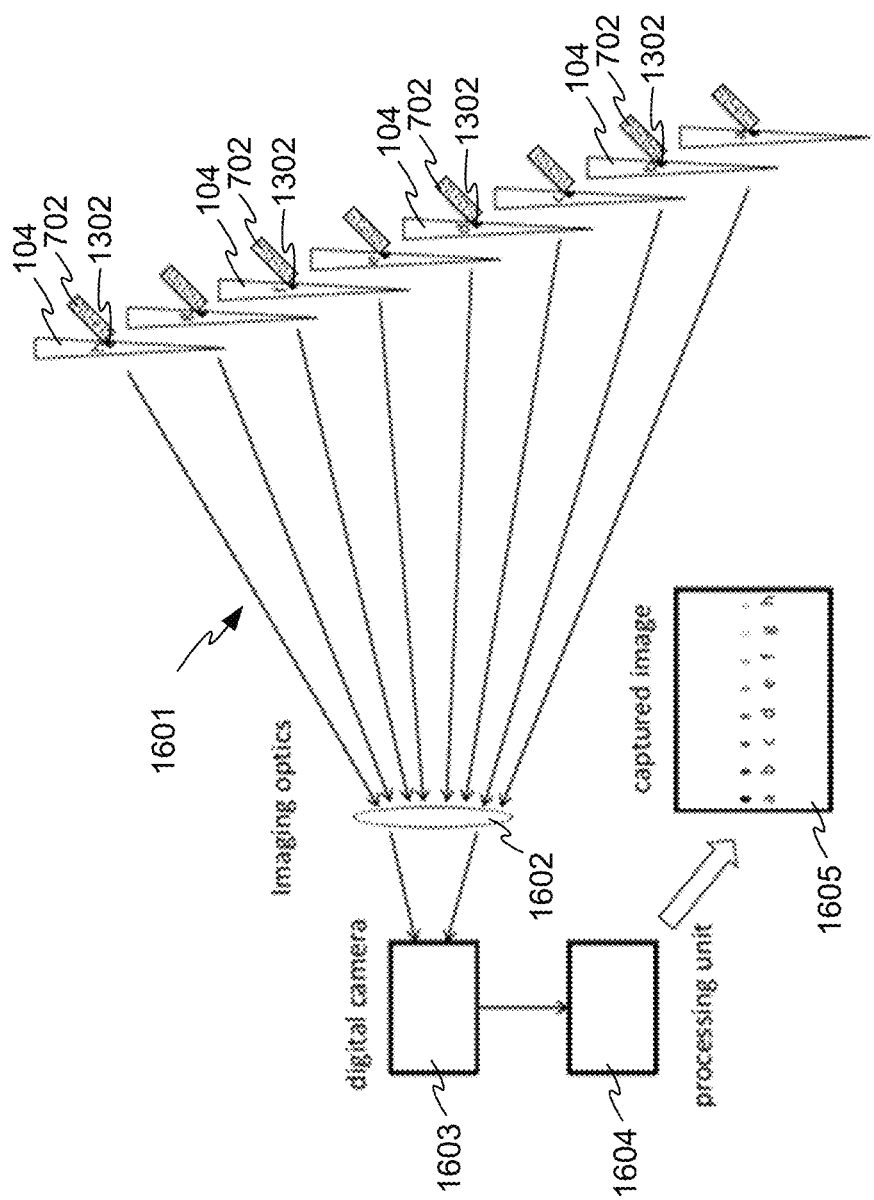
FIG. 16 shows a basic scheme that allows reading of light emitted from a number of pipette tips in a linear arrangement, in accordance with embodiments of the invention.

FIG. 16 shows a basic scheme that allows reading the light emitted from a number of pipette tips 104 in a linear arrangement. A mechanical system (not shown) holds pipette tips 104 in the linear arrangement. For each pipette tip 104, a magnet 702 holds beads in the pipette tip 104 in a clump of beads 1302. (Not all of the tips, magnets, and clumps are labeled in FIG. 16). The markers on the beads emit light 1601, some of which is captured by imaging optics such as a lens 1602. The captured light is directed to an array sensor of a digital camera 1603 and forms an array of spots on the array sensor. Digital camera 1603 which may pass its output to a processing unit for storage, display, and analysis. Digital camera 1603 may contain an area sensor such as a CCD, CMOS or other kind of sensor, that converts incoming light from points in a field of view to electrical signals at corresponding sensor pixels, the signal being proportional to the brightness of the incoming light. The electrical signals can be converted to digital values. As is shown in FIG. 16, the light spots emitted from beads 1302 are imaged at different locations on the sensor of digital camera 1603, so that the resulting image 1605 shows the separate spots. When a spot on the sensor of digital camera 1603 is larger than one pixel, the digital values from a neighborhood of pixels may be averaged to quantify the brightness of the particular spot. In FIG. 16, the different pipette tips 104 are labeled a-h, as are the corresponding spots in digital image 1605, captured by digital camera 1603. This scheme may be implemented using an imager system designed for imaging gels or other biological samples such as the ChemiDoc MP sold by Bio-Rad Laboratories, Inc. In other embodiments, the instrument may include a built-in imaging system to image the light emitting spots within the instrument.

In some embodiments of instrument 100 such as are described above, there can be a two-dimensional array of pipette tips 104, each emitting light. Without further accommodation, it is not possible to directly view all of the light-emitting spots of a two-dimensional array of pipette tips 104. In order to read the results of the assays performed using a two-dimensional array, one option would be to provide every pipette tip 104 with a light sensor, but this would be cumbersome and expensive. Another option would be to design a mechanism that would present the individual rows of the array to an optical system one at a time, as in FIG. 16. However, this would also be cumbersome and expensive, and introduces time lags between measurements of rows, which may introduce errors due different reaction times. It is very desirable to read all of the signals from the two-dimensional array simultaneously.

Figure 17:
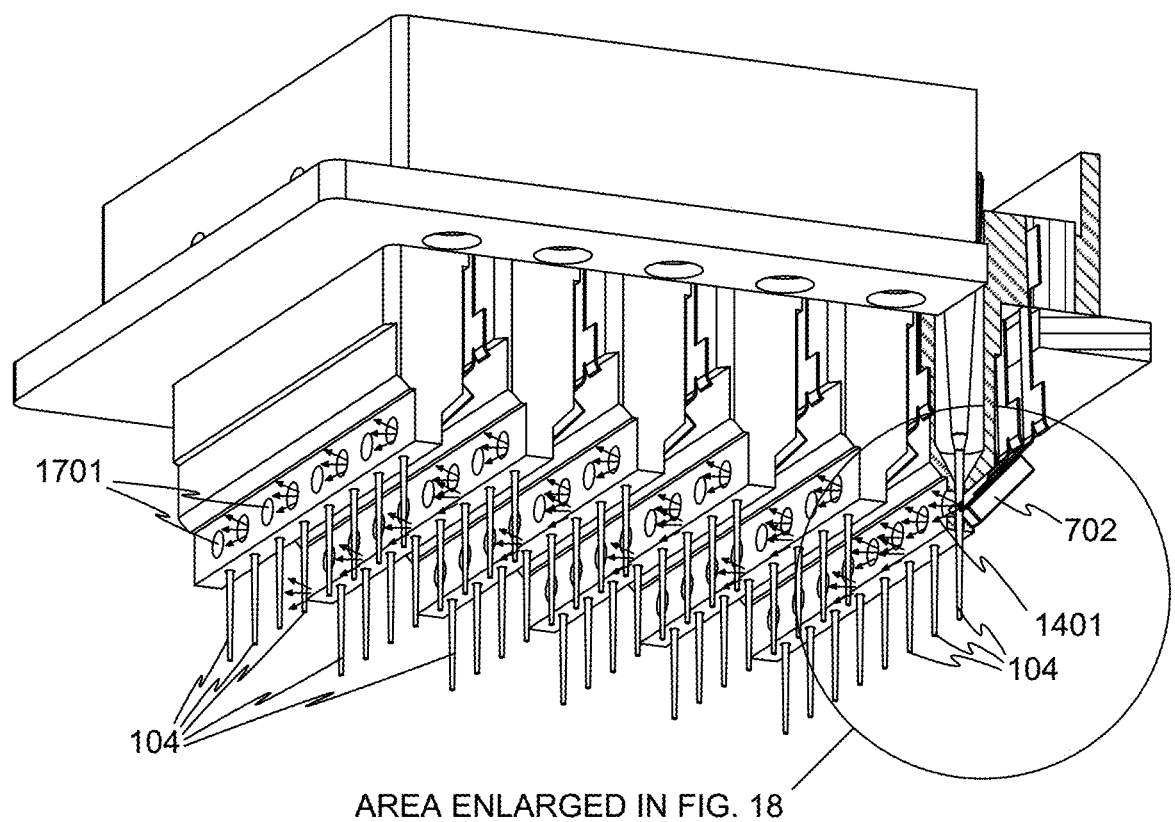
FIG. 17 is a lower oblique view of the magnet module of FIG. 7, partially cutaway, showing apertures in accordance with embodiments of the invention.
Figure 18:
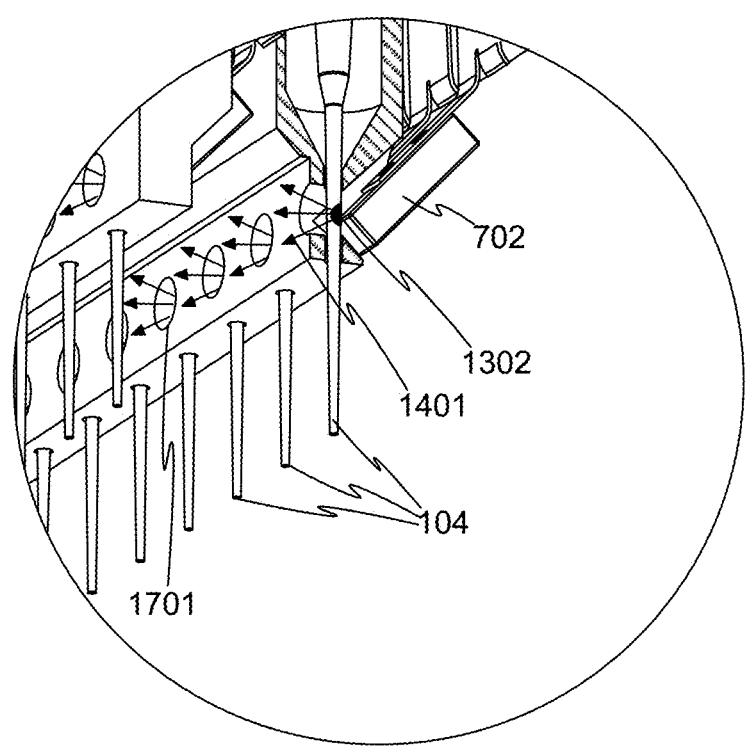
FIG. 18 shows an enlarged view of a portion of FIG. 17.

In order to simultaneously view light being emitted from all of the pipette tips 104, instrument 100 uses a system of one or more mirrors to redirect the light to a viewable direction. This technique is enabled in part by the structure of magnet module 109. FIG. 17 is another lower oblique view of magnet module 109, partially cutaway as in FIG. 8, showing apertures 1701, through which light 1401 from beads 1302 passes. FIG. 18 shows an enlarged view of a portion of FIG. 17. Only some of apertures 1701 are labeled in FIG. 17, and light 1401 is shown passing through only some of them.

Figure 19:
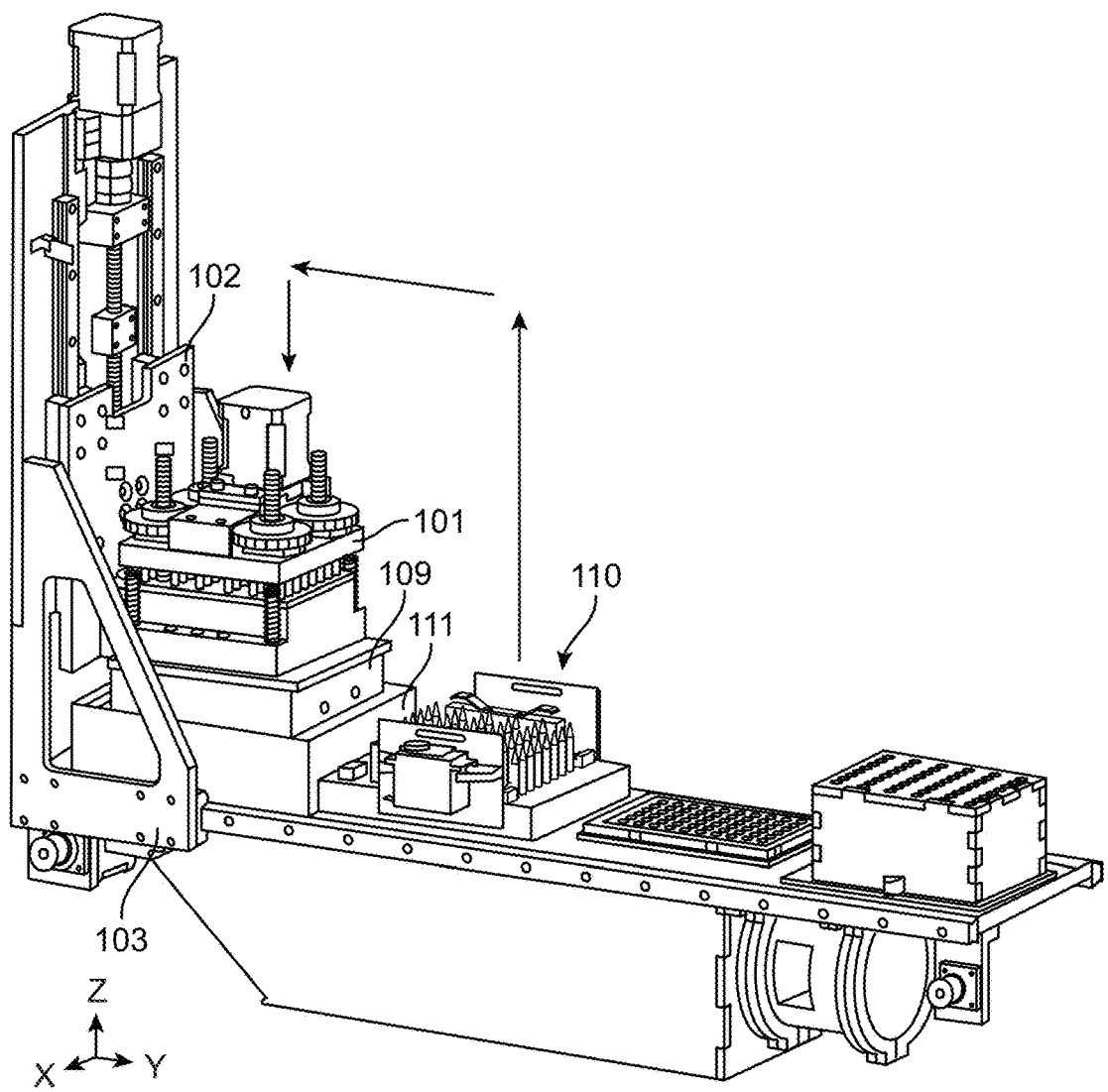
FIG. 19 illustrates another step in performing an assay, in which the pipettor of FIGS. 3A and 3B is placed on a mirror module.
Figure 20:
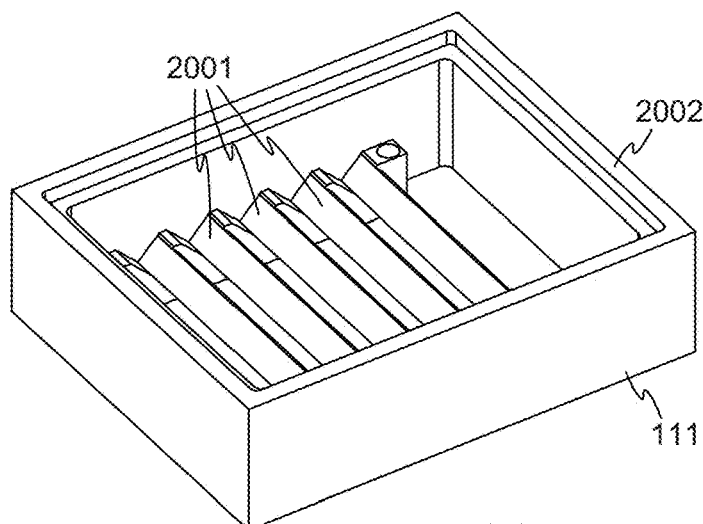
FIG. 20 shows the mirror module of FIG. 19 in isolation.

In order to read light 1401 emanating from the group of pipette tips 104, instrument 100 moves the combined pipettor 101, magnet module 109, and pipette tips 104 onto mirror module 111, as shown in FIG. 19. FIG. 20 shows mirror module 111 in isolation. Mirror module 111 includes a number of angled mirrors 2001. In this example, there are six mirrors 2001, one mirror for each row of pipette tips 104, but in other embodiments, other numbers of mirrors may be present. Mirrors 2001 are preferably surrounded by a light shield 2002. As is visible in FIG. 19, magnet module 109 and mirror module 111 are coupled closely together, and couple closely with the base of instrument 100, so that stray light is substantially prevented from interfering with the reading of the light sources in pipette tips 104.

Figure 21:
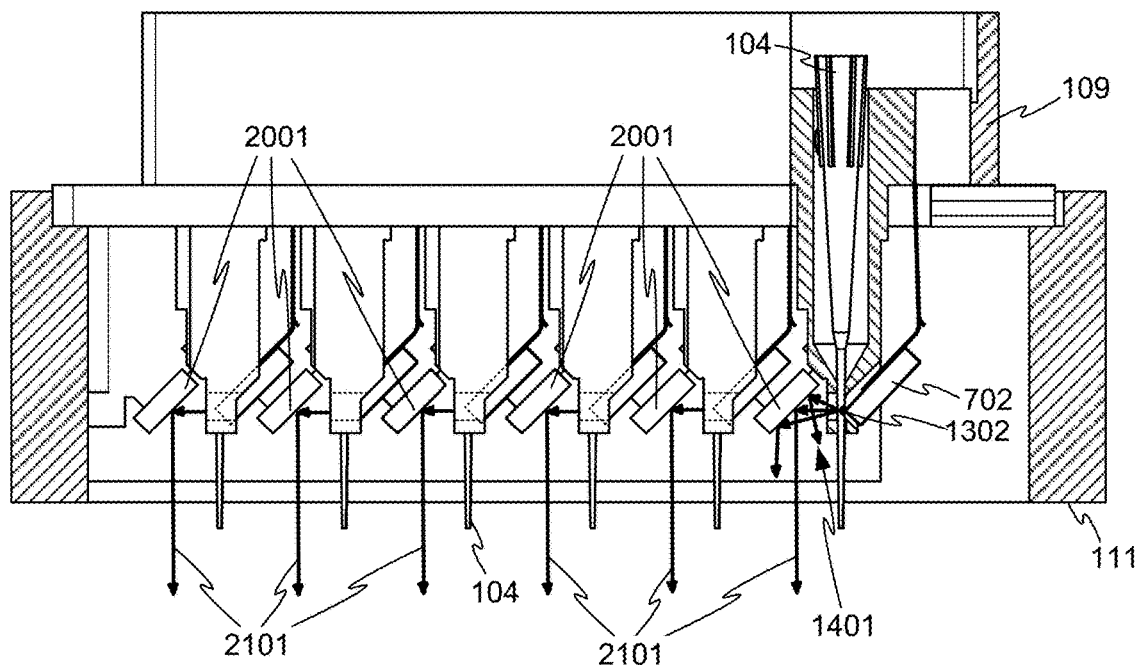
FIG. 21 shows a cutaway orthogonal view of the magnet module, mirror module, and pipette tips, in accordance with embodiments of the invention.

FIG. 21 shows a cutaway orthogonal view of magnet module 109, mirror module 111, and pipette tips 104, from the same perspective as in FIG. 8. Light 1401 from beads 1302 reflects from mirrors 2001, and is directed generally downward, as indicted at 2101. As viewed from below, the concentrated beads 1302 in the various pipette tips 104 appear as a two-dimensional array of light sources.

In one embodiment, the array of light sources can be read by a digital camera positioned below mirror module 111, with the viewing direction of the digital camera aimed directly upward.

Figure 22:
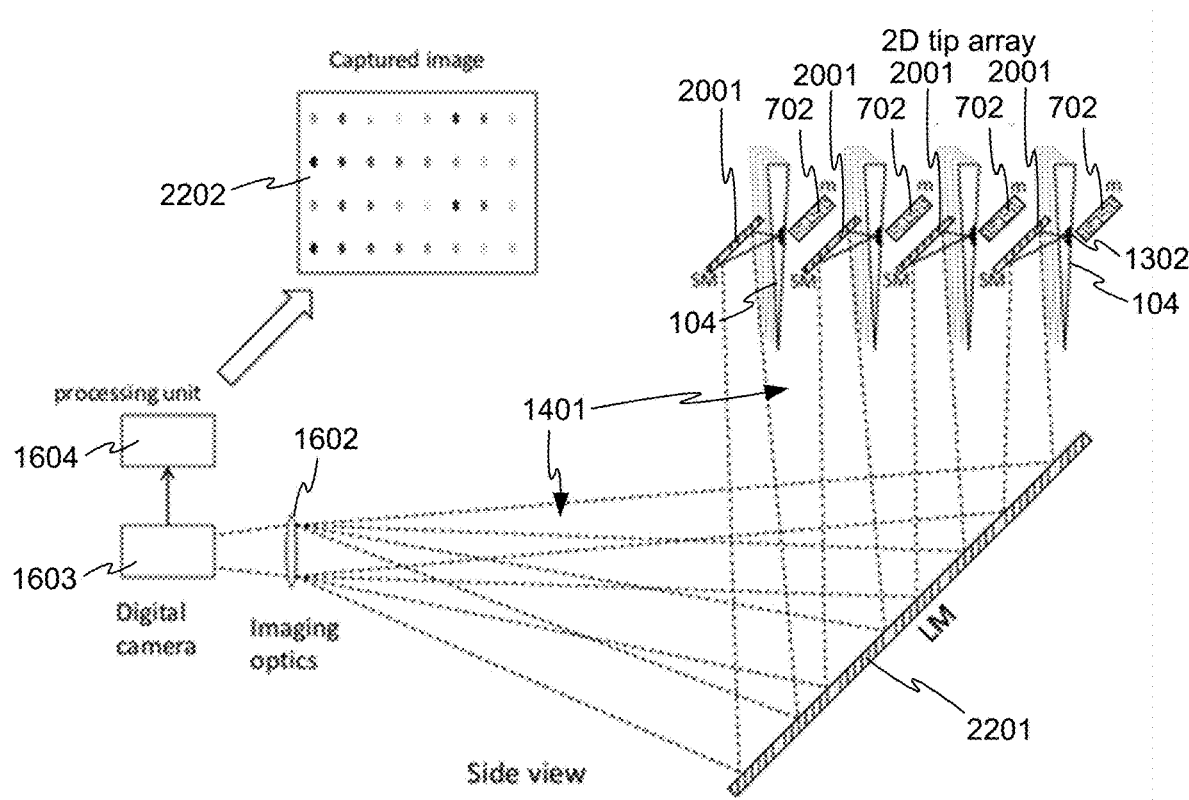
FIG. 22 illustrates the use of a turning mirror, in accordance with embodiments of the invention.

In other embodiments, the overall size of instrument may be reduced by using an additional mirror to further fold the optical path from beads 1302 to a camera used to take an image of the beads. This situation is depicted schematically in FIG. 22. Light 1401 emanating from beads 1302 reflects from mirrors 2001 and is directed generally downward. A larger turning mirror 2201 intercepts the light and reflects it horizontally toward lens or lens system 1602 and a digital camera 1603, which may be similar to the optics and camera described above in the discussion of FIG. 16. The output of the digital camera may be passed to a processing unit 1604 for storage, analysis, and display. Digital image 2202 illustrates the two-dimensional array of light sources as imaged by digital camera 1603.

Figure 23:
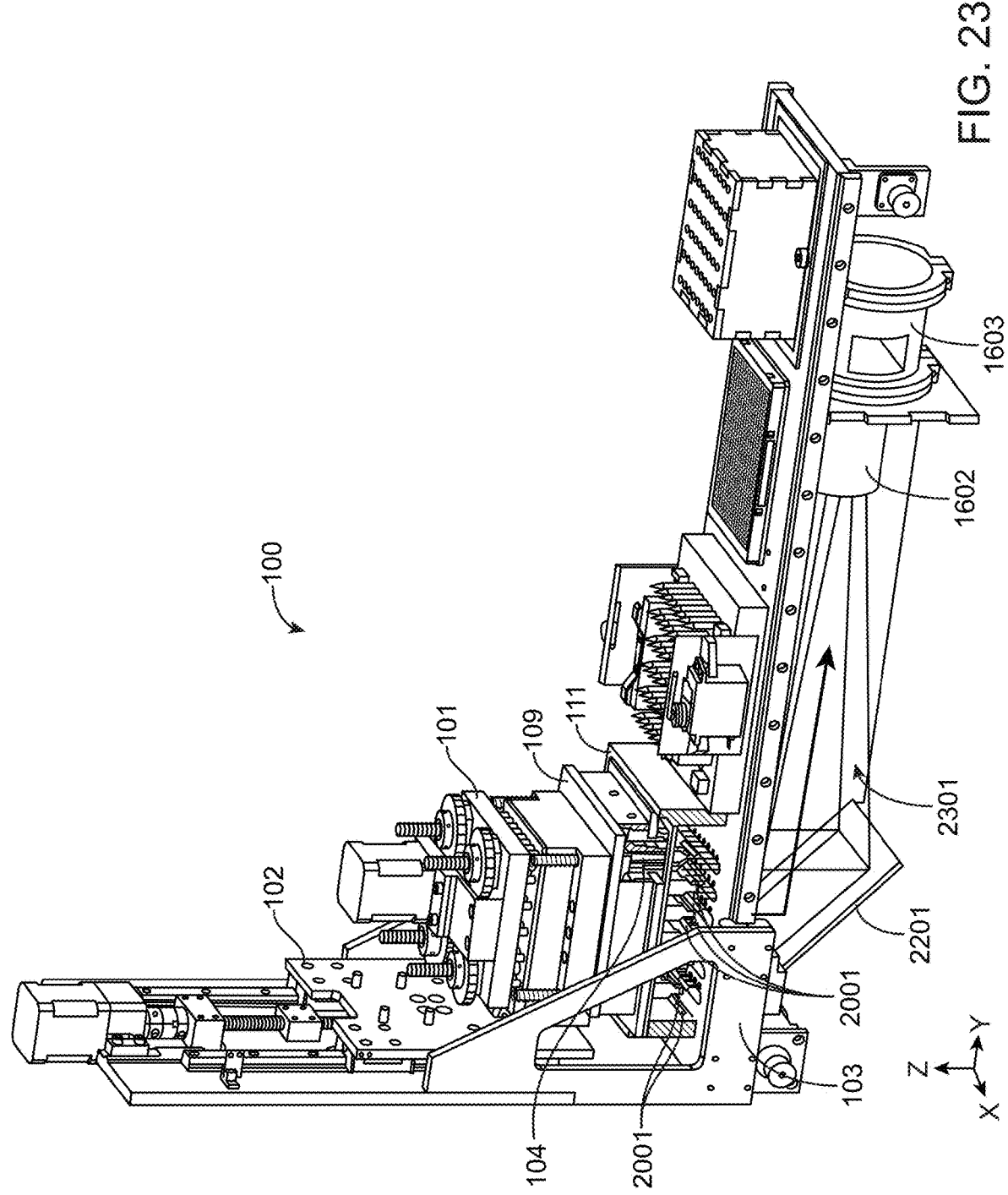
FIG. 23 illustrates a partially cutaway view of the instrument, showing the mounting of the turning mirror under other parts of the system, in accordance with embodiments of the invention.

FIG. 23 illustrates a partially cutaway view of instrument 100, showing the mounting of turning mirror 2201 under the stations on top of the system. Turning mirror 2201 is preferably a first surface mirror, and is large enough to receive light from the entire array of pipette tips 104 and redirect it to optics such as lens 1602, which provides the light to lens or lens system 1602 and digital camera 1603. The light path 2301 is shown in the aggregate for the array of pipette tips 104, for ease of illustration. Turning mirror 2201 may conveniently be placed at a 45-degree angle to the light coming downward from pipette tips 104, so that the turned light path is horizontal, although other arrangements are possible. Turning mirror 2201, placed beneath the rest of instrument 100, can enable a more compact instrument. Multiple turning mirrors may be used, to further reduce the size of the instrument, to allow the use of a lens with a longer focal length, or for other reasons.

Lens 1602 may conveniently be a prime lens having a suitable focal length for imaging the light spots in pipette tips 104 onto the sensor of digital camera 1603. While lens 1602 may have any workable numerical aperture, a larger aperture (a lower f-number) is preferred, for capturing as much optical signal as possible, within the mechanical constraints of the system. For example, lens 1602 may have an f-number of 4.0, 2.8, 2.0, 1.4, 1.2, or another suitable value. In some embodiments, lens 1602 may be a zoom lens.

Other optical components may be present in instrument 100 as well, for example aperture stops, field stops, light shields, polarizers, filters, or other components or combinations of components.

Figure 24:
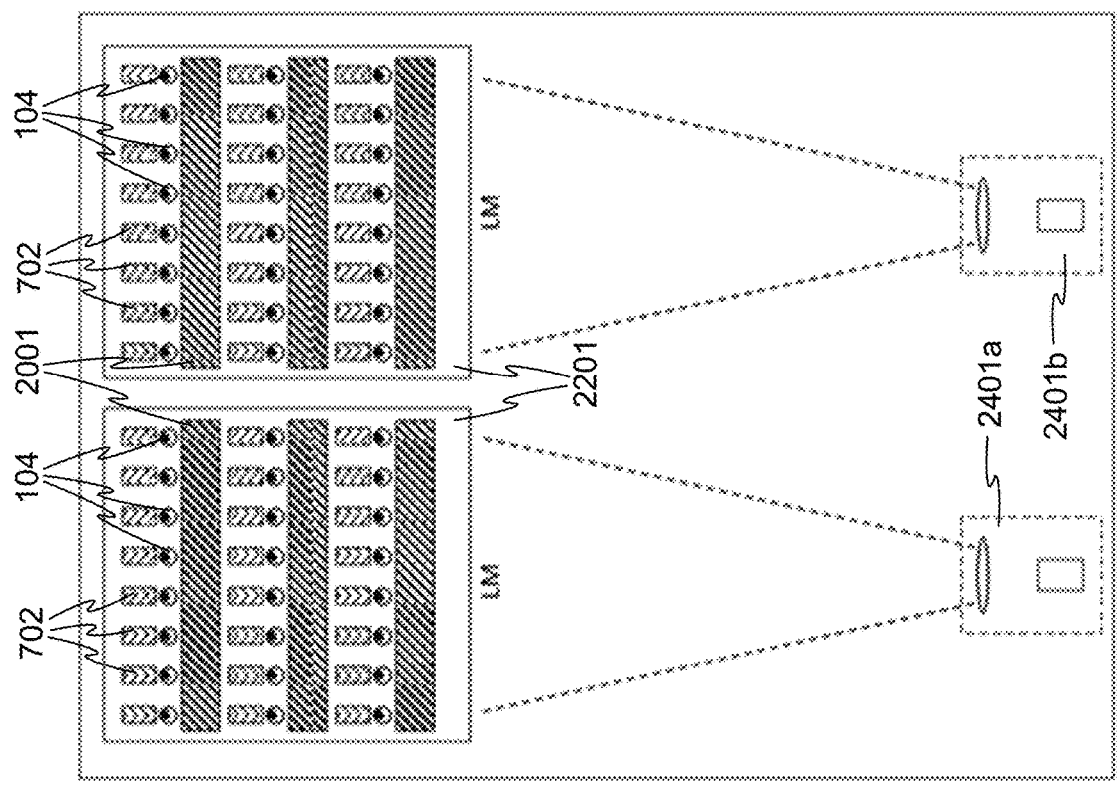
FIG. 24 shows a schematic top view of a system that uses two cameras to image two different subsets of an array of pipette tips, in accordance with embodiments of the invention.

In other embodiments, other techniques may be used for imaging the light sources in the pipette tips. For example, FIG. 24 shows a schematic top view of a system that uses two cameras 2401a and 2401b to image two different subsets of pipette tips 104. While only two arrays of 3×8 pipette tips 104 are shown in FIG. 24, the multi-camera arrangement may enable the use of larger arrays of pipette tips 104. The multi-camera system may simplify the optical design of the system by reducing the required field angles of cameras 2401a and 2401b as compared with a single camera, may provide for greater system throughput, or may have other advantages.

Figure 25:
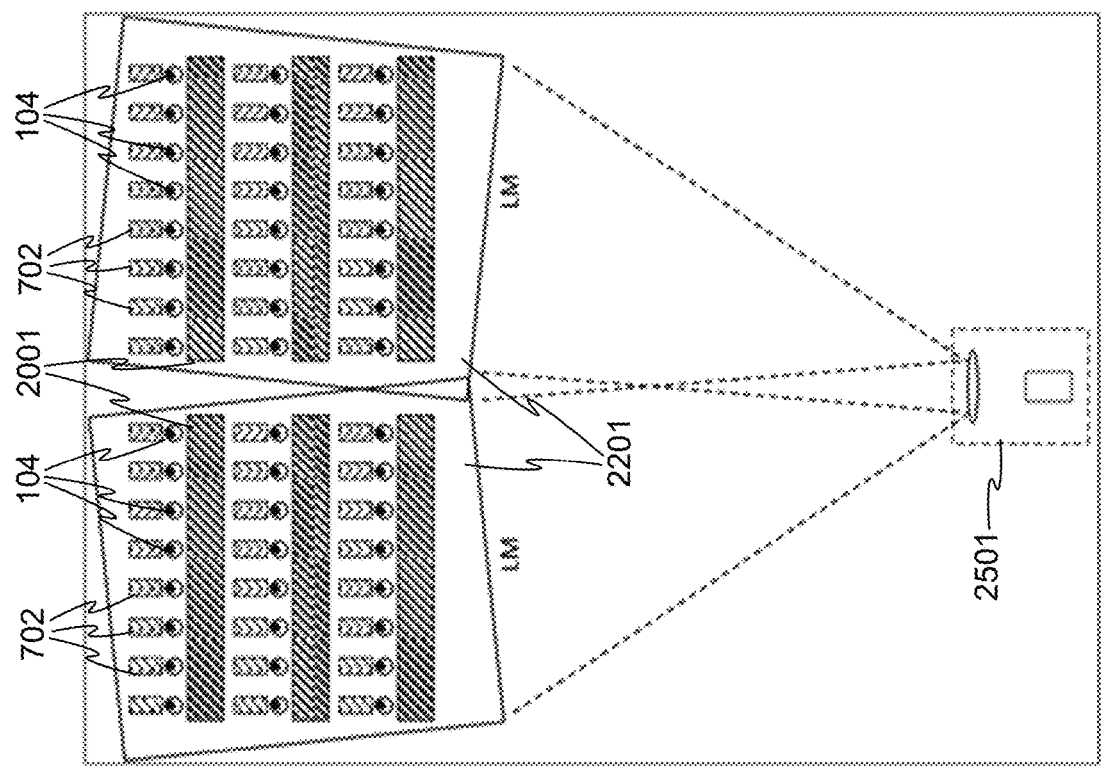
FIG. 25 shows a schematic top view of a system that uses a single cameras to image two different subsets of an array of pipette tips, in accordance with embodiments of the invention.

FIG. 25 illustrates another arrangement in accordance with other embodiments, in which a single camera 2501 is used, but two turning mirrors 2201 can deliver light from two different portions of the array of pipette tips 104. In this example, the two turning mirrors 2201 are rotated slightly, to direct the light from their respective field portions to camera 2501. Camera 2501 can thus "see" both fields of pipette tips 104 at once. In order that the two images will not overlap, and fall one on each other, one or both of turning mirrors 2201 can be tilted slightly from its 45-degree angle. For example, one of turning mirrors 2201 may be tilted slightly higher than 45 degrees, and the other slightly lower. Thus, the spots on the sensor of camera 2501 resulting from the light sources in pipette tips 104 in one part of the field may fall in the dark areas between the spots resulting from the other part of the field. This is possible since only the spots emit light, and the rest of the plate is essentially completely dark, so the dark, unused areas at the camera sensor can be used for the other array. By using one camera rather than two, this arrangement may reduce the cost of the instrument, and reduce power consumption and internal heat buildup, as compared with the two-camera arrangement of FIG. 24.

Figure 26:
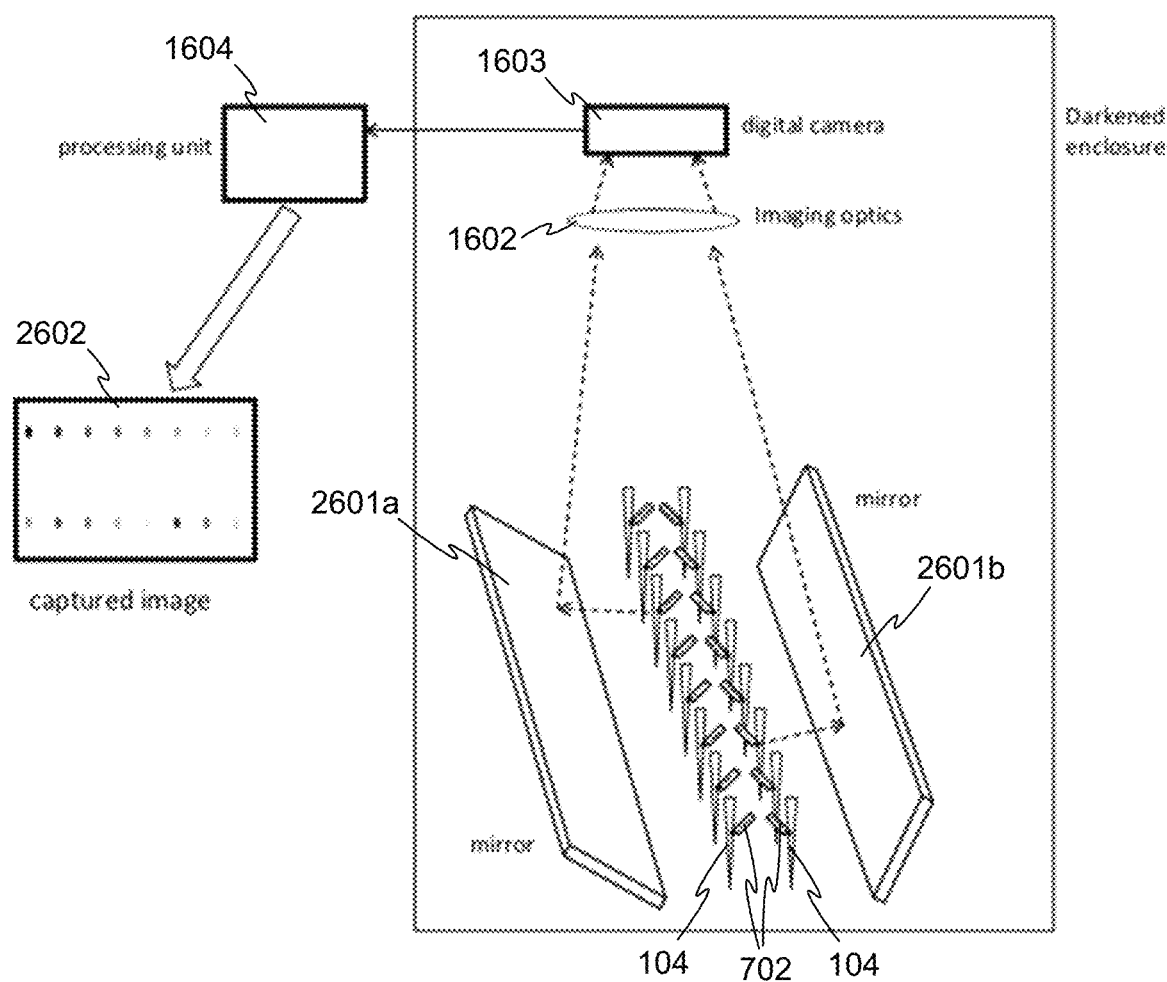
FIG. 26 is a schematic view of an instrument in accordance with other embodiments of the invention.

FIG. 26 is a schematic view of an instrument in accordance with other embodiments. In the embodiment of FIG. 26, two rows of pipette tips 104 and magnets 702 are arranged "back to back", so that light emanates from the two rows in opposite directions. Two turning mirrors 2601a and 2601b are provided, directing the light upward to lens 1602 and digital camera 1603. The image produced by digital camera 1603 is transferred to a processing unit 1604 for storage, display, or analysis. The resulting digital image 2602 shows the two rows of light spots, and indicates the relative intensity of light from each of pipette tips 104. Preferably, the components of the system up to and including at least lens 1602 are enclosed in a darkened enclosure, to exclude ambient light from camera 1603.

The system of FIG. 26 may be implemented using a commercial imager such as the ChemiDoc MP, or ChemiDoc Touch, available from Bio-Rad Laboratories, Inc. The assay and beads manipulation may be carried out apart from the imager, and the pipette tips 104, magnets 702, and mirrors 2601a and 2601b placed in the imager enclosure for the reading step, during the chemiluminescence reaction.

Figure 27:
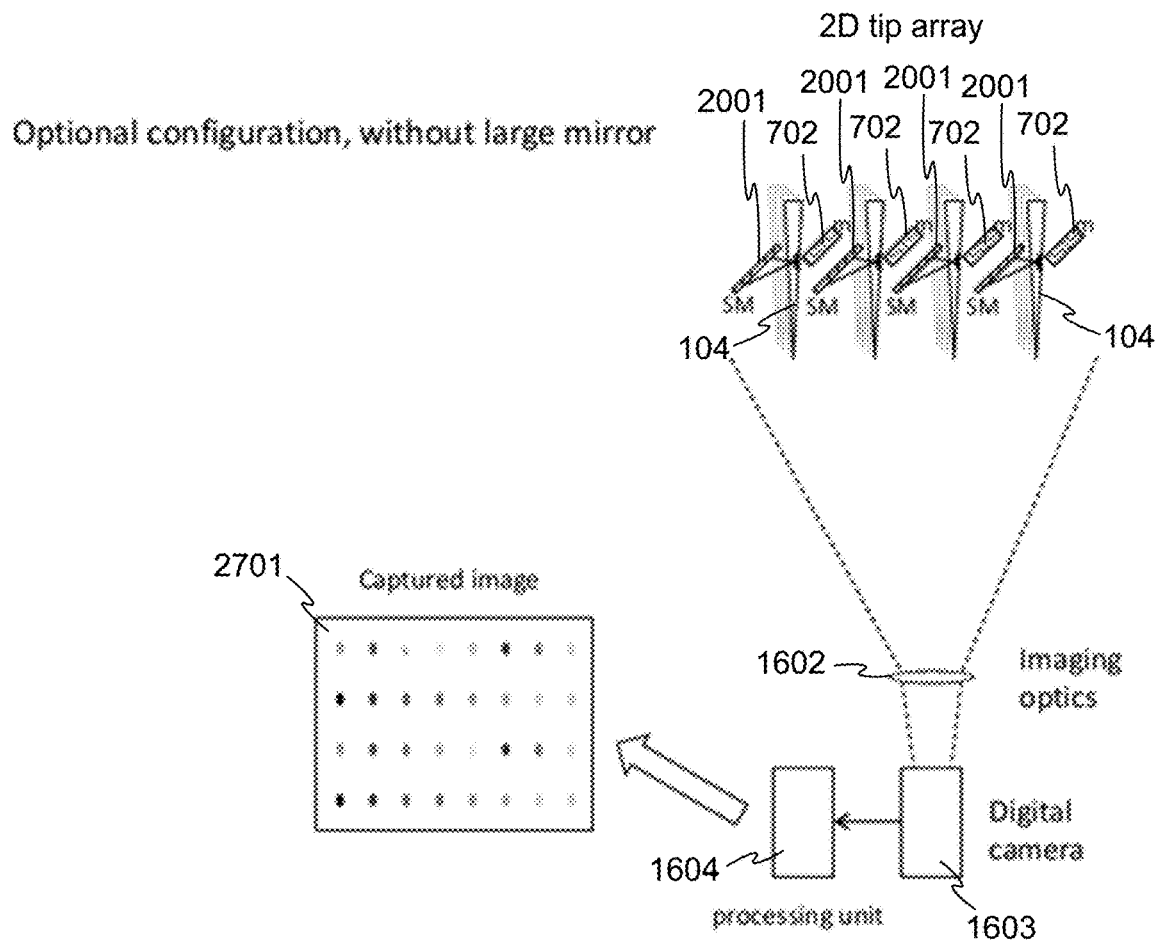
FIG. 27 is a schematic view of an instrument in accordance with other embodiments of the invention.

FIG. 27 is a schematic view of an instrument in accordance with other embodiments, in which no turning mirror 2201 is used, as was suggested above. The operation of the system of FIG. 27 is similar to the operation of the system of FIG. 22. Without any turning mirror 2201, the system of FIG. 27 may be taller than the system of FIG. 22, but may be functionally identical, other than the resulting digital image 2701 being a mirror image of the digital image taken by the system of FIG. 22.

Figure 28:
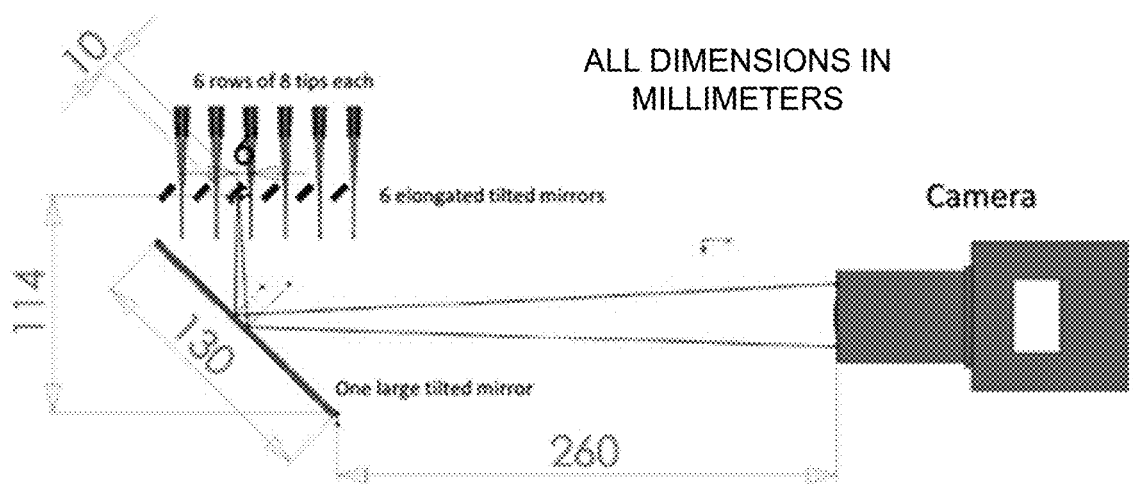
FIG. 28 illustrates a set of workable dimensions for an instrument according to embodiments of the invention.

FIG. 28 illustrates a set of workable dimensions for an instrument according to embodiments of the invention. In other embodiments, other dimensions may be used. The dimensions in FIG. 28 are given in millimeters.

Figure 29:
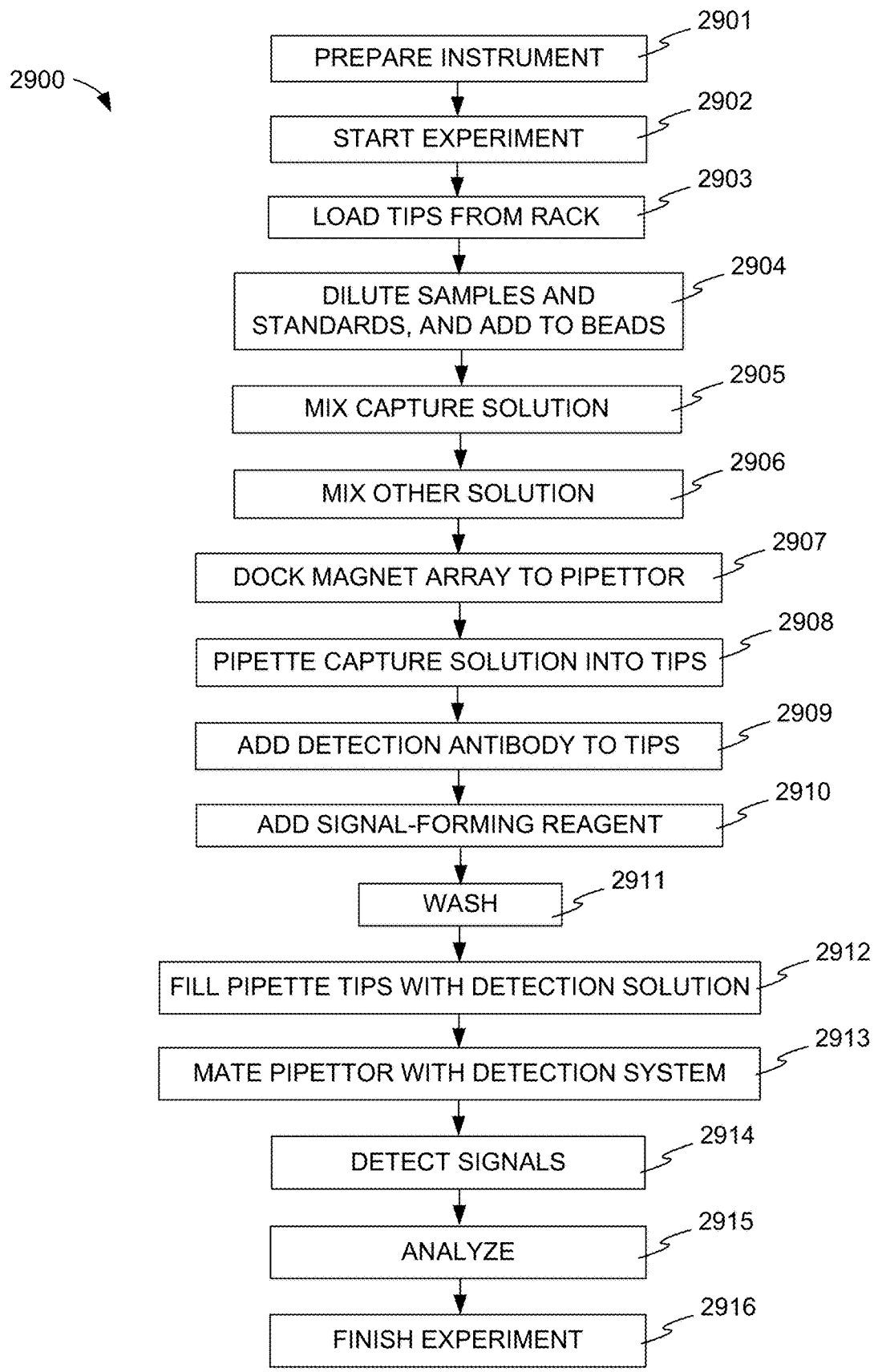
FIG. 29 illustrates a flow chart of a method for performing an assay, in accordance with embodiments of the invention.

FIG. 29 illustrates a flow chart of a method 2900 for performing an assay using an instrument such as instrument 100, in accordance with embodiments of the invention.

In step 2901, a user of the system prepares the instrument. For example, the user may place all of the required disposable components, samples, and standards in position for an assay. This may include loading a set of pipette tips 104 into tip rack 105, placing the solution containing the analyte to be detected in certain wells 201 of reagent plate 107, placing washing fluids in other wells 201 of reagent plate 107, placing magnetic beads in certain wells 201 of reagent plate 107, placing magnet module 109 in magnet module coupling station 110, and other tasks.

In step 2902, the user starts the experiment, for example by pressing a "start" button or selecting a start function from a computer user interface.

In step 2903, the pipette tips 104 are loaded onto pipettor 101 from tip rack 105, by movements of Z-axis mechanism 102 and Y-axis mechanism 103, as is described above.

In step 2904, the samples and standards may be diluted, and added to the magnetic beads. This creates a "capture solution" in at least some of the wells 201 of reagent plate 107. The capture solution includes at least the analyte to be detected or measured, and beads coated with the capture antibody.

In step 2905, the capture solution is mixed, for example by vibrating or rocking the reagent plate 107, or otherwise moving reagent plate 107 or otherwise mixing the capture solution in reagent plate 107. This step is carried out for a period of time long enough to ensure good capture. In some embodiments, the mixing may go on for an hour or more, for example in assays with a relatively low concentration of analyte in the capture solution.

In step 2906, additional solutions may be added and/or mixed by the pipettor. An example is mixing of two components of a reagent which are provided separately to extend their shelf life. Optionally, the tips are replaced after this step, so new tips are used from step 2907 and on. Steps 2905 and 2906 may be performed in parallel if desired, which may save time.

In step 2907, the magnet array 109 is docked to the pipettor 101, using movements of Z-axis mechanism 102 and Y-axis mechanism 103, as is described above.

In step 2908, the capture solution is loaded into pipette tips 104 using pipettor 101. Because the solution contains the magnetic beads, and the magnet array 109 is in place next to pipette tips 104, the beads holding the analyte to be detected or measured are concentrated next to the respective magnets. Excess capture solution may be expelled if desired, and washing solution may be loaded and expelled if desired.

In step 2909, the detection antibody is loaded into pipette tips 104 using pipettor 101, from additional wells 201 of reagent plate 107. The detection antibody is held in pipette tips 104 for a sufficient amount of time to allow the detection antibody to bind with the analyte held to the magnetic beads. Because the detection antibody can be supplied in relatively high concentration, the holding time may be shorter than the time required for allowing the analyte to bind to the capture antibody, although different experiments will require different holding times, and any relative amounts of time are possible. Excess detection antibody solution may be expelled if desired, and washing solution may be loaded and expelled if desired.

In step 2910, reagents for signal formation are loaded into pipette tips 104 using pipettor 101, for example from additional wells 201 of reagent plate 107. The signal-forming reagents may include fluorescent tags or enzymes that catalyze chemiluminescent reaction. For example, when the detection antibody is biotin-labeled, a signal-forming reagent may include streptavidin-HRP, in which HRP (horseradish peroxidase) is capable of catalyzing luminol/hydrogen peroxide reaction for chemiluminescence formation. The reagents are held in pipette tips 104 for a time sufficient for the detectable tags to bind to the magnetic beads. Excess reagent solution may be ejected if desired, and washing solution may be loaded and ejected if desired.

In some embodiments, step 2910 may be optional, for example if the detection antibody is pre-labeled with a signal forming tag. In some embodiments, the detection antibody is labeled with biotin, and in this step labeled avidin (or derivative) is bound.

In step 2911, excess solutions are removed from pipette tips 104 and the tips are washed, using the pipettor and washing solutions from reagent plate 107. However, it will be recognized that washing steps may be performed at any workable and helpful point in the experiment process, and that in some embodiments, step 2911 may be obviated by washing steps performed at other times.

In an optional step 2012, the pipette tips 104 may be filled with a detection solution, for example luminol-hydrogen peroxide or another suitable solution.

In step 2913, pipettor 101 (still holding pipette tips 104, magnet module 109, and the analyte-coated beads), is docked with the detection system at mirror module 111.

In step 2914, signals from the detectible tags on the beads are read by the detection system. For example, light from the beads in pipette tips 104 may be reflected downward by mirrors 2001 to turning mirror 2201, and then to lens 1602 and camera 1603.

In step 2915, the signals are analyzed, for example by processing unit 1604.

In step 2916, the experiment may be finished, for example by returning magnet module 109 to magnet module coupling station 110, ejecting pipette tips 104 from pipettor 101, and discarding the disposable items used in the experiment.

It will be recognized that the steps of method 2900 are given as an example, and that variations are possible. The steps may be performed in any workable order.

EXPERIMENTAL

Figure 30:
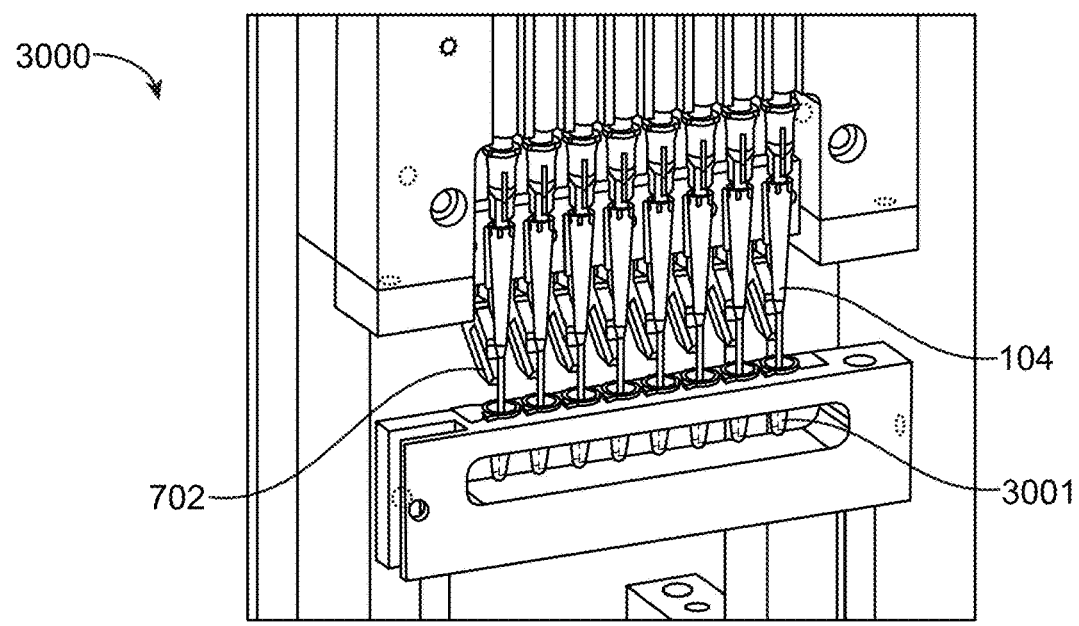
FIG. 30 illustrates a fluid handling system in accordance with embodiments of the invention.
Figure 31:
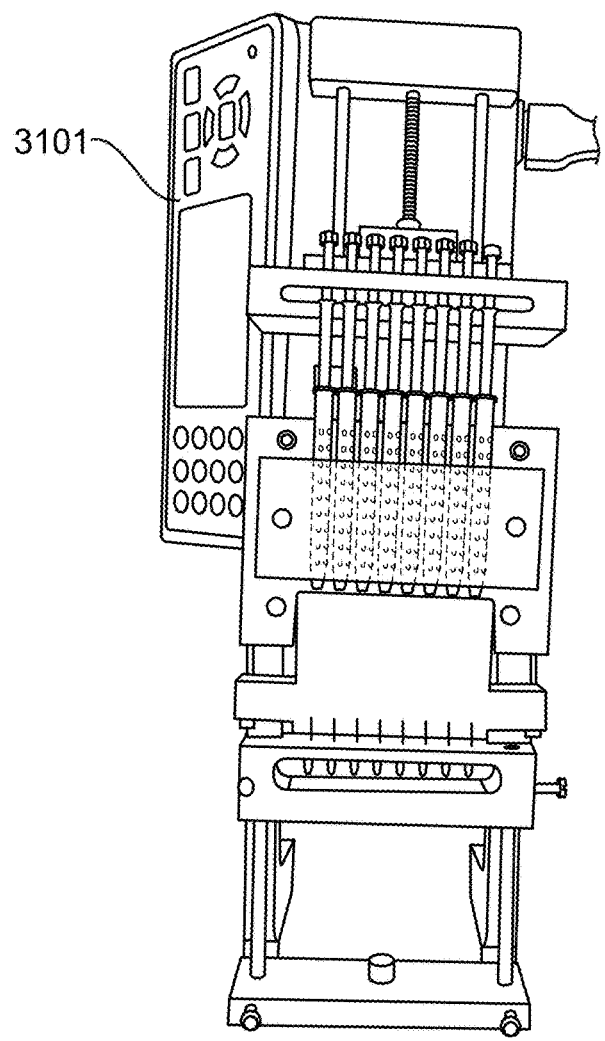
FIG. 31 illustrates the fluid handling system of FIG. 30, mounted with a syringe pump.

To demonstrate the performance of an embodiment of the invention, including the use of folded optics, a fluid handling system 3000 was built, as shown in FIG. 30, having eight wells 3001, eight pipette tips 104, and eight magnets 702. A photograph of the system is shown in FIG. 31, mounted with a syringe pump 3101, for performing the function of pipettor 101. Samples were prepared as follows:

1. Capture: Standard analyte solution—9 ul at known concentration in standard diluent (contains 25% bovine serum) —was added to 3 ul beads solution. The capture solutions were mixed by placing the vial strip which contains them on an orbital shaker, operated at constant shaking rate for 1 h.
2. Blocking: The tips were filled with PBST for 1 h, in parallel to the capture step.
3. Beads loading: The capture solutions were aspirated to the tips, so the beads are focused to a spot near the magnet.
4. Detection antibody: The detection antibody solution was aspirated to the tips and held there for 50 min.
5. StreptAvidin-HRP: The SA-HRP solution was aspirated to the tips and held there for 30 min.
6. Chemiluminescence formation: A commercial solution comprising luminol and hydrogen peroxide (Clarity Max from Bio-Rad) was aspirated to the tips and held there for 5 min.
7. Imaging: The system, without the pump head, was taken to the ChemiDoc MP imager and placed in the folded optics model set up, as in FIG. 26. The signals were imaged by the camera of the imager, and their intensity was analyzed using its built-in ImageLab software.

Between steps 2-6, wash steps were performed. Each wash step consisted of passing wash buffer at least two times over the spot.

In order to demonstrate measurement of IL-2 analyte in a wide range of concentrations, seven IL-2 concentrations were used, as shown in Table 1 below. This is in addition to one blank channel (no added analyte).

TABLE 1

| IL-2 (pg/ml)* | Signal Intensity** |
|---|---|
| 48,320 | 524,070 |
| 4,027 | 344,422 |
| 252 | 79,186 |
| 16 | 6,280 |
| 3.9 | 1,590 |
| 0.98 | 592 |
| 0.25 | 450 |
| 0 | 0 |

Figure 32:
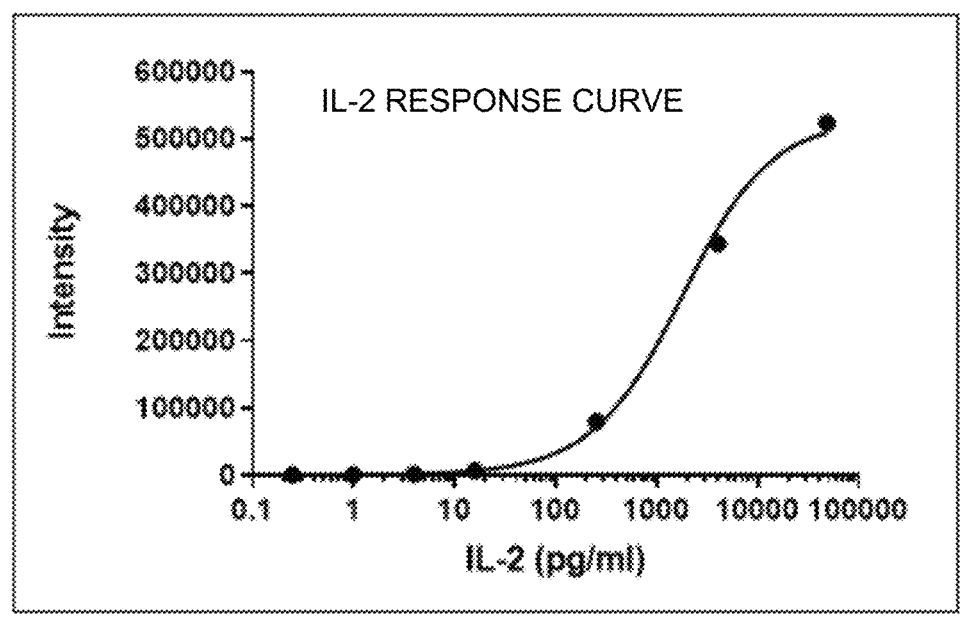
FIG. 32 shows a response curve for measurements of Interleukin 2 (IL-2), in accordance with embodiments of the invention.

*Calculated as concentration in the serum
Exposure time = 2 seconds, after blank signal subtraction These results are plotted in FIG. 32**.

In order to assess the limit of detection (LOD) for the IL-2 model, three analyte concentrations were used, as shown in Table 2 below. These concentrations were at the lower linear range of the calibration curve, in addition to three blank channels (no added analyte).

TABLE 2

| IL-2 (pg/ml)* | Signal Intensity** |
|---|---|
| 3.9 | 2,033 |
| 0.98 | 597 |
| 0.98 | 727 |
| 0.25 | 237 |
| 0.25 | 245 |
| 0 | −9 |
| 0 | −7 |
| 0 | 17 |

Figure 33:
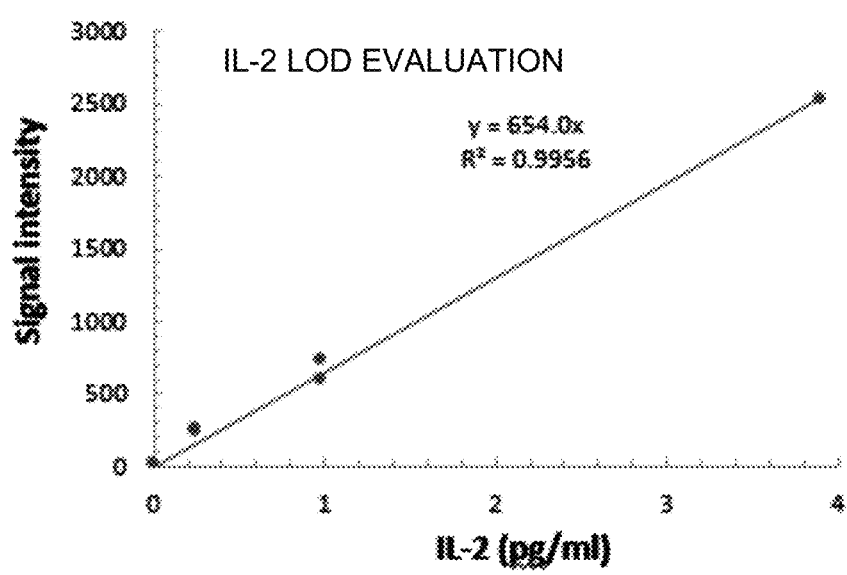
FIG. 33 shows a linear portion of the response curve of FIG. 32.

*Calculated as concentration in the serum
Exposure time = 2 seconds, after blank signal subtraction LOD was calculated as the concentration that gives a signal of 3 standard deviations of the measured blank signals, using a linear fit as shown in FIG. 33. From Table 2 above, the standard deviation of the readings taken a zero concentration (−9, −7, 17) is 14.47. Three times this standard deviation is 3×14.47=43.40, which from the graph in FIG. 33** corresponds to an IL-2 concentration of 0.066 pg/ml (43.40/654).

Similar experiments were conducted to demonstrate measurement of IL-6 analyte in a wide range of concentrations. Seven IL-6 concentrations were used, as shown in Table 3 below. This is in addition to one blank channel (no added analyte).

TABLE 3

| IL-6 (pg/ml)* | Signal Intensity** |
|---|---|
| 58,000 | 264,080 |
| 19,333 | 246,880 |
| 3,867 | 172,350 |
| 773 | 76,580 |
| 155 | 20,090 |
| 31 | 4,590 |
| 6.2 | 505 |
| 0 | 0 |

Figure 34:
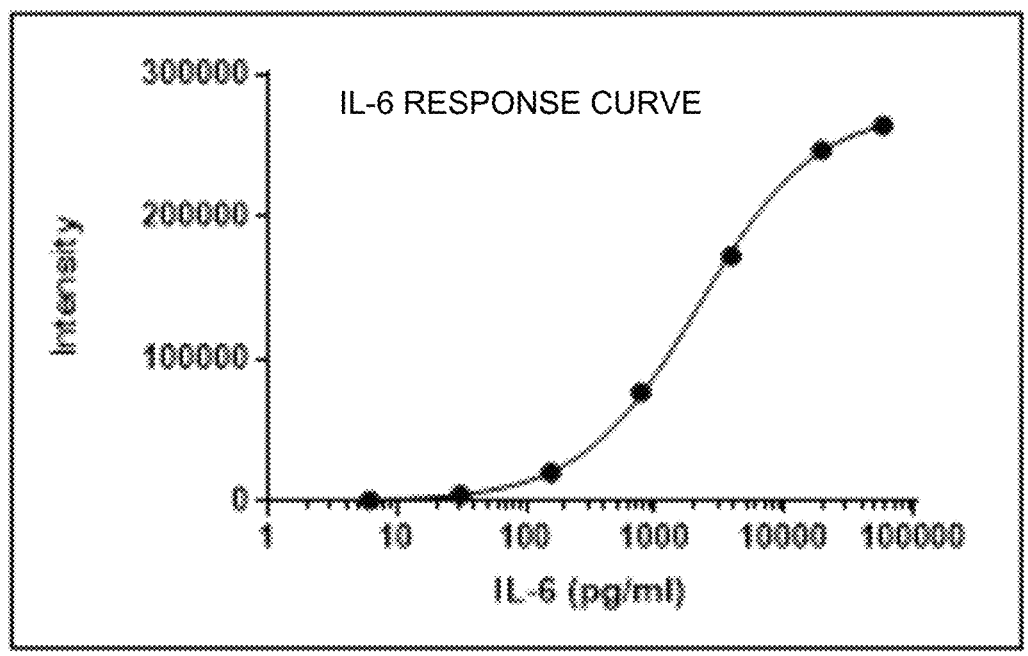
FIG. 34 shows a response curve for measurements of Interleukin 6 (IL-6), in accordance with embodiments of the invention.

*Calculated as concentration in the serum
Exposure time = 2 seconds, after blank signal subtraction These results are plotted in FIG. 34**.

In order to assess the limit of detection (LOD) for the IL-6 model, three analyte concentrations were used, as shown in Table 4 below. These concentrations were at the lower linear range of the calibration curve, in addition to three blank channels (no added analyte).

TABLE 4

| IL-6 (pg/ml)* | Signal Intensity** |
|---|---|
| 17 | 2,411 |
| 4.3 | 768 |
| 4.3 | 545 |
| 1.1 | 151 |
| 1.1 | 189 |
| 0 | −21 |
| 0 | 3 |
| 0 | 18 |

Figure 35:
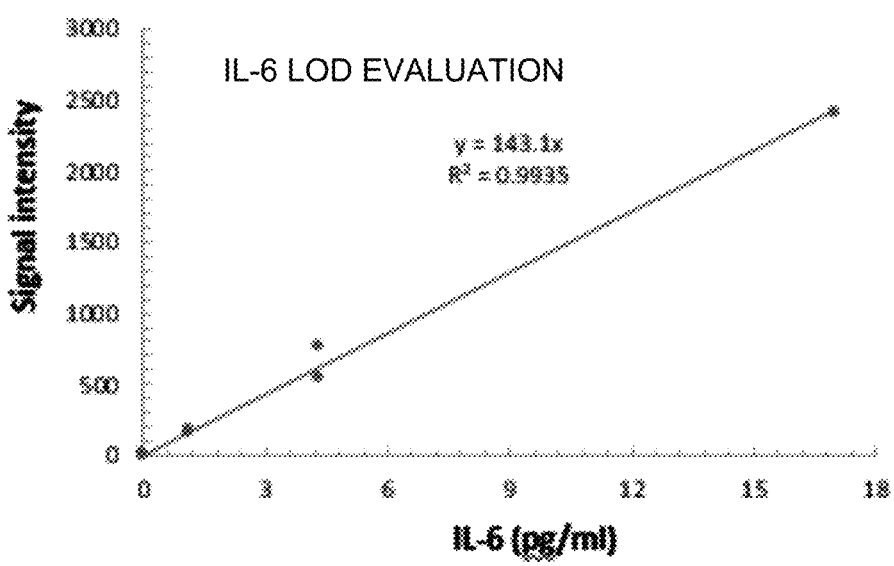
FIG. 35 shows a linear portion of the response curve of FIG. 34.

*Calculated as concentration in the serum
**Exposure time = 2 seconds, after blank signal subtraction LOD was calculated as the concentration that gives a signal of 3 standard deviations of the measured blank signals, using a linear fit as shown in FIG. 35. From Table 4 above, the standard deviation of the readings taken a zero concentration (−21, 3, 18) is 19.67. Three times this standard deviation is 3×19.67=59.01, which from the graph in FIG. 35 corresponds to an IL-6 concentration of 0.412 pg/ml (59.01/143.1).

Those of skill in the art will recognize that an LOD below 1 pg/ml represents a very sensitive assay, as compared with previous techniques. Similarly, the dynamic range of the system, as measured by the ratio of the maximum measurable signal to the LOD is very high, and is greater than $1 \times 10^5$ in each of the above examples.

It will be apparent to those skilled in the art that various modifications and variations can be made in the method and system of the present invention without departing from the spirit or scope of the invention. Thus, it is intended that the present invention include modifications and variations that are within the scope of the appended claims and their equivalents. It is to be understood that any workable combination of the features and capabilities disclosed herein is also considered to be disclosed.

What is claimed is:

1. An instrument for detecting signal from a biological sample, the instrument comprising:
a pipettor module configured to hold a plurality of pipettes in respective pipette positions, each of the pipette positions having an associated pipette tip position, to hold liquid in one or more pipette tips, and to pipette liquid in and out of the one or more pipette tips, each of the one or more pipette tips having a pipette tip point;
one or more magnets positioned such that each of the one or more pipette tips is adjacent to one of the one or more magnets;
an optical detection module positioned to detect an optical signal from particles magnetically fixed to respective sides of the one or more pipette tips by the one or more magnets; and
one or more mirrors positioned such that the optical signal from each of the one or more pipette tips is reflected from one of the one or more mirrors and directed at an angle substantially parallel to the orientation of the pipette tips and in the direction of the pipette tip points.

2. The instrument of claim 1, wherein the instrument comprises exactly one magnet for each pipette tip position.

3. The instrument of claim 1, wherein the optical signals are reflected directly from the one or more mirrors to the optical detection module without any further reflections.

4. The instrument of claim 1, wherein the one or more mirrors are one or more first mirrors, the instrument further comprising:
a second mirror positioned under the pipette tip points that redirects the optical signal from the one or more first mirrors to the optical detection module.

5. The instrument of claim 4, wherein the instrument comprises two or more second mirrors, each of the two or more second mirrors reflecting optical signal from a subset of the pipette tips.

6. The instrument of claim 4, wherein the optical detection module comprises a camera positioned to receive optical signal reflected from the second mirror.

7. The instrument of claim 4, wherein the optical detection module has only one camera positioned to receive optical signal originating from each of the one or more pipette tips.

8. The instrument of claim 4, wherein the optical detection module has a plurality of cameras, wherein each of the plurality of cameras is positioned to receive optical signal originating from only a subset of the pipette tips.

9. The instrument of claim 4, wherein there are fewer first mirrors than pipette tip positions, and at least some of the first mirrors reflect optical signal from more than one of the one or more pipette tips.

10. The instrument of claim 1, comprising a plurality of pipette tips disposed in a line or in a two-dimensional array, wherein the pipettor module is configured to hold and pipette liquid in and out of the one or more of pipette tips simultaneously.

11. An instrument for detecting signal from a biological sample, the instrument comprising:
a pipettor module configured to hold a plurality of pipettes in respective pipette positions, each of the pipette positions having an associated pipette tip position, to hold liquid in one or more pipette tips, and to pipette liquid in and out of the one or more pipette tips, each of the one or more pipette tips having a pipette tip point;
one or more magnets positioned such that each of the one or more pipette tips is adjacent to one of the one or more magnets;
a magnet module, wherein the magnet module comprises one or more spring clips, one spring clip respectively for each of the one or more magnets, the one or more spring clips positioned to hold the one or more magnets against the pipette tips; and
a magnet module coupling station where the magnet module is coupled to the pipettor module, the magnet module coupling station comprising one or more posts positioned to deflect the one or more magnets away from the one or more pipettes against the action of the one or more spring clips during coupling of the magnet module to the pipettor module.

12. The instrument of claim 11, further comprising a motorized mechanism configured to move the pipettor module into and out of the magnet module coupling station to automatically couple the magnet module to the pipettor module.

13. The instrument of claim 12, further comprising:
one or more optical detection modules positioned to detect an optical signal from particles magnetically fixed to respective sides of the one or more pipette tips by the one or more magnets; and
one or more mirrors positioned such that the optical signal from each of the one or more pipette tips is reflected from one of the one or more mirrors and directed at an angle substantially parallel to the orientation of the pipette tips and in the direction of the pipette tip points, the one or more mirrors disposed at a detection station;

wherein the motorized mechanism is further configured to move the coupled pipettor module and magnet module to the detection station.

14. The instrument of claim 12, further comprising a reagent loading station, and wherein the motorized mechanism is further configured to move the pipettor module to the reagent loading station.

15. The instrument of claim 14, further comprising a shaker for agitating liquids present at the reagent loading station.

* * * * *